(12) United States Patent
Dean

(10) Patent No.: US 8,921,045 B2
(45) Date of Patent: Dec. 30, 2014

(54) FLUORESCENT COLOR MARKERS

(75) Inventor: Neta Dean, Stony Brook, NY (US)

(73) Assignee: The Research Foundation for The State University of New York, Albany, NY (US)

(*) Notice: Subject to any disclaimer, the term of this patent is extended or adjusted under 35 U.S.C. 154(b) by 29 days.

(21) Appl. No.: 12/393,983

(22) Filed: Feb. 26, 2009

(65) Prior Publication Data

US 2009/0286244 A1  Nov. 19, 2009

Related U.S. Application Data

(60) Provisional application No. 61/031,536, filed on Feb. 26, 2008.

(51) Int. Cl.
| | | |
|---|---|---|
| *C12Q 1/68* | (2006.01) | |
| *C12N 15/81* | (2006.01) | |
| *G01N 33/50* | (2006.01) | |
| *C07K 14/435* | (2006.01) | |

(52) U.S. Cl.
CPC .............. *C12N 15/815* (2013.01); *C12N 15/81* (2013.01); *G01N 33/5023* (2013.01); *C07K 14/43595* (2013.01)
USPC ........................................................ 435/6.12

(58) Field of Classification Search
None
See application file for complete search history.

(56) References Cited

U.S. PATENT DOCUMENTS

| | | |
|---|---|---|
| 6,090,919 A | 7/2000 | Cormack et al. |
| 7,157,566 B2 | 1/2007 | Tsien et al. |
| 7,314,736 B2 | 1/2008 | Remington et al. |
| 2005/0196768 A1 | 9/2005 | Campbell et al. |

OTHER PUBLICATIONS

Sheff et al. (2004) yeast vol. 21: 661-670.*
Rare codon analysis SEQID No. 1 printed Jul. 2013.*
Rare codon analysis SEQID No. 3 printed Jul. 2013.*
Codon usage yeast Sep. 2013.*
Al, H. et al., "Exploration of New Chromophore Structure Leads to Identification of Improved Blue Fluorescent Proteins", Biochemistry (2007), vol. 46, pp. 5904-5910.
Anderson, K. I. et al., "A New Configuration of the Zeiss LSM 510 for Simultaneous Optical Separation of Green and Red Fluorescent Protein Pairs", International Society for Analytical Cytology (2006), Part A, vol. 69A, pp. 920-929.
Bender, A. et al., "Use of a screen for synthetic lethal and multicopy suppressee mutants to identify two new genes involved in morphogenesis in *Saccharomyces cerevisiae*", Mol. Cell. Biol. (1991), vol. 11:3, pp. 1295-1305.
Bevis, B. J. et al., "Rapidly maturing variants of the Discosoma red fluorescent protein (DsRed)", Nature Biotechnology (2002), vol. 20, pp. 83-87.
Brown, A. J. P. et al., "Codon utilisation in the pathogenic yeast, *Candida albicans*", Nucleic Acids Research (1991) vol. 19:15, pp. 4298.
Campbell, R. E. et al., "A monomeric red fluorescent protein", Proc. Nat'l. Acad. Sci. USA (2002), vol. 99:12, pp. 7877-7882.

(Continued)

*Primary Examiner* — Suchira Pande
(74) *Attorney, Agent, or Firm* — Kenyon & Kenyon LLP

(57) ABSTRACT

The invention provides a yeast-enhanced red fluorescent protein. In an embodiment of the invention, the yeast-enhanced red fluorescent protein is monomeric and is expressible in *Candida albicans*. The invention also provides a novel visible color marker for plasmid expression in yeast, particularly *Saccharomyces cerevisiae* and *Candida albicans*.

15 Claims, 10 Drawing Sheets

(56) References Cited

OTHER PUBLICATIONS

Janke, C. et al., "A versatile toolbox for PCR-based tagging of yeast genes new fluorescent proteins, more markers and promotor substitution cassettes". Yeast (2004) vol. 21: pp. 947-962.

Cormack, B. P. et al., "Yeast-enhanced green fluorescent protein (yEGFP): a reporter of gene expression in *Candida albicans*". Microbiology (1997) vol. 143: 303-311.

Crampin, H. et al., "*Candida albicans* hyphae have a Spitzenkorper that is distinct from the polarisome found in yeast and pseudohyphae". Journal of Cell Science (2005) vol. 118: pp. 2935-2947.

Erickson, M.G. et al., "DsRed as a Potential FRET Partner with CFP and GFP". Biophysical Journal (2003) vol. 85, pp. 599-611.

Giepmans, B. N. et al., "The Fluorescent Toolbox for Assessing Protein Location and Function", Science (2006) vol. 312, pp. 217-224.

Gross, L. A. et al., "The Structure of the chromophore within DsRed, a red fluorescent protein from coral", Proc. Nat'l. Acad. Sci. USA (2000) vol. 97:22, pp. 11990-11995.

He, L. et al., "Determination of tumor necrosis factor receptor-associated factor trimerization in living cells by CFP→YFP→mRFP FRET detected by flow cytometry", Nucleic Acids Research (2005), vol. 33:6, pp. e61, pp. 1-12.

Hieter, P. et al., "Mitotic stability of yeast chromosomes: A colony color assay that measures nondisjunction and chromosome loss", Cell (1985), vol. 40, pp. 381-392.

Koshland, D. et al., "Genetic analysis of the mitotic transmission of minichromosomes", Cell (1985), vol. 40, pp. 393-403.

Lloyd, T. et al., "Evolution of codon usage patterns: the extent and nature of divergence between *Candida albicans* and *Saccharomyces cerevisiae*", Nucleic Acids Research (1992), vol. 20:20, pp. 5289-5295.

Matz, M. V. et al., "Fluorescent proteins from nonbioluminescent *Anthozoa* species", Nature Biotechnology (1999), vol. 17, pp. 969-973.

Pearson, W. R. et al., "Improved tools for biological sequence comparison", Proc. Natl. Acad. Sci. USA (1998), vol. 85, pp. 2444-2448.

Rida, P. C. G., et al., "Yeast-to-Hyphal Transition Triggers Formin-dependent Golgi Localizatin to the Growing Tip in *Candida albicans*", Mol. Biol. Cell (2006), vol. 17, pp. 4364-4378).

Robinson, J. S. et al., "Protein sorting in *Saccharomyces cerevisiae*: isolation of mutants defective in the delivery and processing of multiple vacuolar hydrolases", Molecular and Cellular Biology (1988), vol. 8:11, pp. 4936-4948.

Rockmill, B. et al., "Spore enrichment", Methods Enzymol. (1991), vol. 194, pp. 146-149.

Roman, H., "Studies of gene mutation in *Saccharomyces*", Cold Spring Harb Symp Quant Biol (1956), vol. 21: pp. 175-185.

Sharp, P. M. et al., "Codon usage patters in *Escherichia coli, Bacillus subtilis, Saccharomyces, cerevisiae, Schizosaccharomyces pombe, Drosophila melanogaster* and *Homo sapiens*; a review of the considerable within-species diversity", Nucleic Acids Research (1988), vol. 16:17, pp. 8207-8211.

Shaner, N. C. et al., "Improved monomeric red, orange and yellow fluorescent proteins derived from *Discosoma* sp. red fluorescent protein", Nature Biotech (2004), vol. 22:12, pp. 1567-1572.

Sikorski, R.S. et al., "A System of Shuttle Vectors and Yeast Host Strains Designed for Efficient Manipulation of DNA in *Saccharomyces cerevisiae*", Genetics (1989), vol. 122, pp. 19-27.

Slaughter, B. D. et al., "Mapping dynamic protein interactions in MAP kinase signaling using live-cell fluorescence fluctuation spectroscopy and imaging". PNAS (2007), vol. 104:51, pp. 20320-20325.

Sprague, G. F, "Assay of yeast mating reaction", Methods in Enzymology (1991), vol. 194, pp. 77-93.

Su, W. W., "Fluorescent proteins as tools to aid protein production", Microbial Cell Factories (2005), vol. 4:12.

Thomas, B. J, et al., "The genetic control of direct-repeat recombination in *Saccharomyces*: the effect of rad52 and rad1 on mitotic recombination at GAL10, a transcriptionally regulated gene", Genetics (1989), vol. 123, pp. 725-738.

Smith, T. "Going Green", Nature Structural Biology (2000), vol. 7:12, p. 1089.

Wall, M. A. et al., "The structural basis for red fluorescence in the tetrameric GFP homolog DsRed", Nat. Struc. Biol. (2000), vol. 7:12. pp. 1133-1138.

Wang, L. et al., "Evolution of new nonantibody proteins via iterative somatic hypermutation", PNAS (2004), vol. 101:48, pp. 16745-16749.

Warenda, A. J. et al., "Septin Function in *Candida albicans* Morphogenesis", Mol. Bio. Cell (2002), vol. 13, pp. 2732-2746.

Fischer, M. et al., "A brilliant monomeric red fluorescent protein to visualize cytoskeleton dynamics in *Dictyostelium*", FEBS Letters (2004), vol. 577, pp. 227-232.

Wilson, R. B. et al., "Rapid hypothesis testing with *Candida albicans* through gene disruption with short homology regions", J. Bacteriol. (1999) vol. 181:6, pp. 1868-1874.

Yarbrough, D. et al., "Refined crystal structure of DsRed, a red fluorescent protein from coral, at 2.0-1 resolution", Proc. Nat'l Acad. Sci USA (2001) vol. 98:2, pp. 462-467.

Yoko, T, et al., "Differences in in vivo acceptor specificity of two galactosyltransferases, the gmh3+ and gma12+ gene products from *Schizosaccharomyces pombe*", Eur. J. Biochem. (1998), vol. 257, pp. 630-637.

* cited by examiner

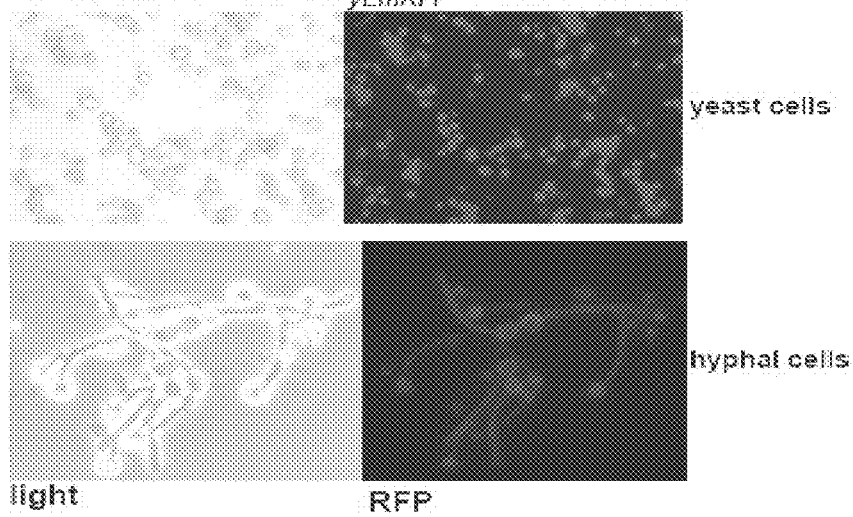
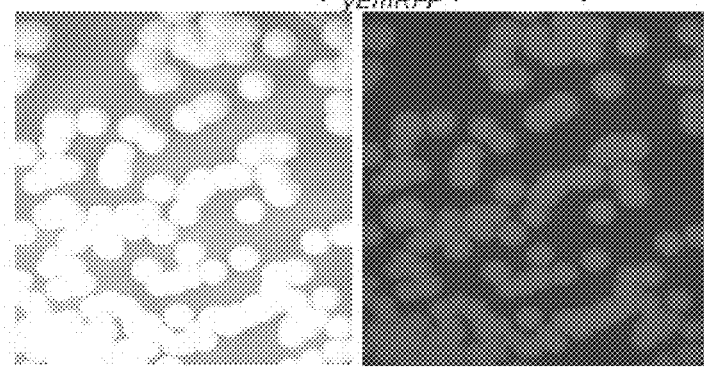
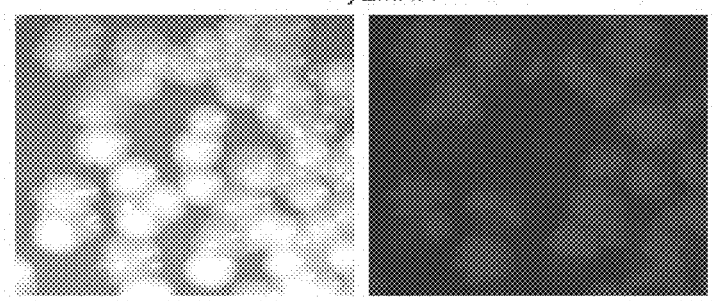
Fig. 1

A.
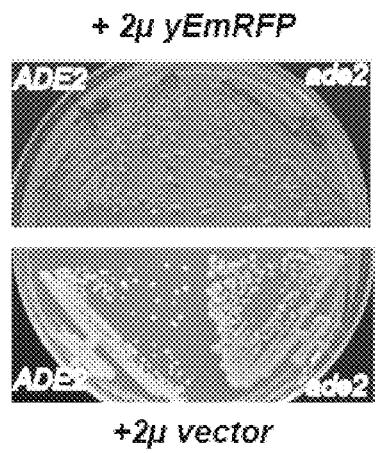
B.
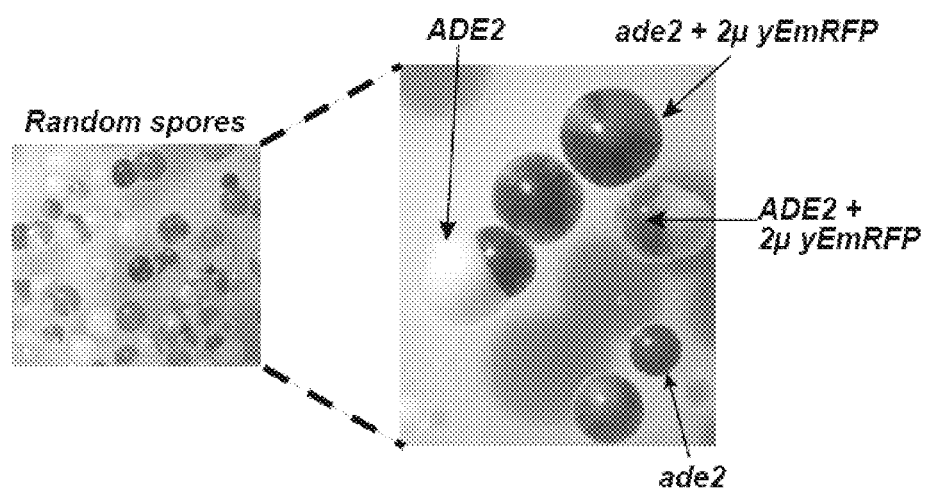
C.
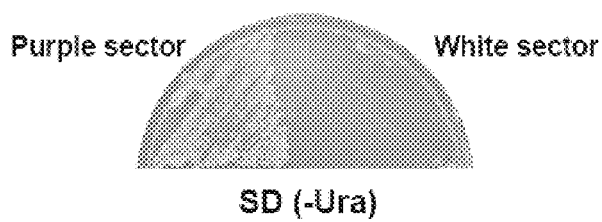
Fig. 2

FIG. 5

| CODON | AMINO ACID | yEmRFP | mRFP | CODON | AMINO ACID | yEmRFP | RFP |
|---|---|---|---|---|---|---|---|
| TCT | S | 0 | 0 | TAT | Y | 12 | 0 |
| TCC | S | 0 | 11 | TAC | Y | 0 | 12 |
| TCA | S | 12 | 0 | TAA | - | 1 | 1 |
| TCG | S | 0 | 0 | TAG | - | 0 | 0 |
| AGT | S | 0 | 0 | TGA | - | 0 | 0 |
| AGC | S | 0 | 1 | CAT | H | 6 | 0 |
| ATT | I | 10 | 0 | CAC | H | 0 | 6 |
| ATC | I | 0 | 10 | CAA | Q | 8 | 0 |
| ATA | I | 0 | 0 | CAG | Q | 0 | 8 |
| ATG | M | 10 | 10 | AAT | N | 7 | 0 |
| GTT | V | 15 | 0 | AAC | N | 0 | 7 |
| GTC | V | 0 | 2 | AAA | K | 24 | 0 |
| GTA | V | 0 | 1 | AAG | K | 0 | 24 |
| GTG | V | 0 | 12 | GAT | D | 14 | 1 |
| TTA | L | 7 | 0 | GAC | D | 0 | 13 |
| TTG | L | 6 | 2 | GAA | E | 24 | 2 |
| CTT | L | 0 | 0 | GAG | E | 0 | 22 |
| CTC | L | 0 | 0 | TGT | C | 0 | 0 |
| CTA | L | 0 | 0 | TGC | C | 0 | 0 |
| CTG | L | 0 | 11 | CGT | R | 0 | 0 |
| CCT | P | 0 | 1 | CGC | R | 0 | 6 |
| CCC | P | 0 | 11 | CGA | R | 0 | 0 |
| CCA | P | 12 | 0 | CGG | R | 0 | 1 |
| CCG | P | 0 | 0 | AGA | R | 8 | 0 |
| ACT | T | 12 | 0 | AGG | R | 0 | 1 |
| ACC | T | 0 | 12 | GGT | G | 25 | 1 |
| ACA | T | 0 | 0 | GGC | G | 0 | 24 |
| ACG | T | 0 | 0 | GGA | G | 0 | 0 |
| GCT | A | 11 | 1 | GGG | G | 0 | 0 |
| GCC | A | 0 | 10 | TTT | F | 10 | 0 |
| GCA | A | 0 | 0 | TTC | F | 0 | 10 |
| GCG | A | 0 | 0 | TGG | W | 3 | 3 |

Fig. 6

FLUORESCENT COLOR MARKERS

CROSS REFERENCE TO RELATED APPLICATIONS

This application claims priority to U.S. Application No. 61/431,536, filed Feb. 26, 2008, which is incorporated herein by reference in its entirety.

FEDERAL FUNDING

This invention was produced in part using funds obtained through grant RO1-GM048467 from the National Institutes of Health. The federal government has certain rights in this invention.

FIELD OF THE INVENTION

The present invention relates to novel red fluorescent proteins. The red fluorescent proteins are functional in yeasts, particularly *Candida albicans*, and *Saccharomyces cerevisiae*, and further provide color markers visible under natural light.

BACKGROUND OF THE INVENTION

*Candida albicans* is an important human pathogen This fungus is a member of the normal body flora but under certain conditions, for instance when there is a defect in immunity, *C. albicans* is no longer benign. Instead it becomes a dangerous pathogen that colonizes different tissues, causing grave illness and death. *C. albicans* is a major concern in hospitals where it is increasingly being identified as the causal agent in nosocomial infections. As yet, there are few effective drugs against *C. albicans*.

*C. albicans* has a diploid genome and no known sexual cycle. Consequently, although *C. albicans* is of great scientific interest, classical genetic studies have been very challenging. Furthermore, modern genetic reporter systems have been hampered by the difficulties in heterologous protein expression in *C. albicans*. Expression of yeast-enhanced green fluorescent protein in *C. albicans* has been reported (Cormack et al., Yeast-enhanced green fluorescent protein (yEGFP): a reporter of gene expression in *Candida albicans*. Microbiology 143: 303-311 (1997)), but additional fluorescent markers that are well expressed in yeast, particularly in *C. albicans*, and useful for analysis of expression, protein localization, protein-protein interaction, and the like are desired.

Red fluorescent protein (RFP) was first isolated and sequenced from a *Discosoma* sp. (see, e.g., Matz et al., Nature Biotech. 17:969 973 (1999), Gross et al, Proc. Nat'l. Acad. Sci. USA 97:11990 11995 (2000)). The crystal structure of red fluorescent protein shows it to be a tetrameric protein (Wall et al., Nat. Struc. Biol. 7:1089 (2000); Yarbrough et al., Proc. Nat'l Acad. Sci. USA 16:462-467 (2000)). A humanized variant RFP has also been engineered (Clontech, "DsRED™").

RFP, like other fluorescent proteins, is useful as a reporter molecule for a variety of bioassays. Directed mutagenesis experiments that led to development of the bright monomeric mRFP variants used a DsRFP template (DsRed-N1) that had been codon-optimized for expression in human cells (Bevis, et al., Rapidly maturing variants of the *Discosoma* red fluorescent protein (DsRed). Nature Biotech. 20: 83-87 (2002); Campbell et al., A monomeric red fluorescent protein. Proc. Nat'l. Acad. Sci. USA 99: 7877-7882 (2002)). The monomeric variants of the tetrameric *Discosoma* sp. RFP are widely used as fluorescent protein tags in mammalian cells, but are not well expressed in *S. cerevisiae* and other yeast and fungi with. AT-rich genomes, and expression in *C. albicans* of RFP has not been possible thus far.

SUMMARY OF THE INVENTION

The present invention provides an isolated nucleic acid sequence that encodes a yeast-enhanced red fluorescent protein (yeRFP), expressible in *Candida albicans*. In one embodiment, the red fluorescent protein is a chromoprotein that can be detected visually under natural light. In another embodiment, the isolated nucleic acid sequence encodes a fusion protein. In another embodiment, the yeast-enhanced red fluorescent protein is a monomeric RFP (mRFP).

In an embodiment of the present invention, a yeast-enhanced red fluorescent protein is provided that is at least about 70%, about 80%, about 90%, or about 95% identical to SEQ ID NO:2. The invention encompasses yeast enhanced red fluorescent proteins which though similar in amino acid sequence, are characterized by a variety of UV excitation and emission wavelengths and/or display different colors when viewed under natural light. Non limiting examples of the yeast-enhanced red fluorescent proteins fluoresce red, orange, yellow, or blue. In an embodiment of the invention, the yeast-enhanced red fluorescent protein is a mutant optimized for FACS. In another embodiment of the invention the yeast-enhanced red fluorescent protein is encoded by a nucleic acid comprising SEQ ID NO:1, SEQ ID NO:3, SEQ ID NO:5, SEQ ID NO:7, or SEQ ID NO:9.

In still another embodiment, the nucleic acid encoding a yeast-enhanced red fluorescent protein hybridizes under stringent conditions to a nucleotide sequence selected from the group consisting of SEQ ID NO:1, SEQ ID NO:3, SEQ ID NO:5, SEQ ID NO:7, and SEQ ID NO:9.

In another embodiment, the isolated nucleic acid comprises an expression control sequence which provides expression that is, for example, constitutive, inducible, or developmental stage specific. Accordingly, the invention also provides host cells, such as fungal and bacterial host cells, comprising yeast-enhanced red fluorescent protein nucleic acids. The host cells can be pathogenic or nonpathogenic. In one embodiment, the host cell is *C. albicans*. In another embodiment, the host cell is *S. cerevisiae*. In another embodiment, the host cell is useful for genetic manipulation of the yeast-enhanced red fluorescent protein nucleic acids, e.g., *E. coli*.

The invention provides a vector which comprises a nucleic acid of the present invention that encodes a yeast-enhanced red fluorescent protein. In a further embodiment, a host cell comprises the vector. In still further applications, the host cell is *C. albicans* or *S. cerevisiae* or *E. coli*.

In one embodiment, a yeast cell is analyzed by a method that includes the steps of expressing a nucleic acid encoding a yeast-enhanced red fluorescent protein in the cell and observing expression of the yeast-enhanced red fluorescent protein. In certain embodiments, the yeast cell is an *S. cerevisiae* or *C. albicans* cell.

In still further embodiments, the analysis method is carried out by monitoring color, fluorescence, or temporal or spatial changes in color or fluorescence. Color or fluorescence can be monitored visually, or determined with the aid of, for example, a fluorimeter or spectrophotometer. Such analyses may comprise the step of sorting the yeast cell according to its color or fluorescence, using, for example, fluorescence activated cell sorting (FACS). In one analytical method, a nucleic acid encodes a protein of interest or a fragment thereof fused to a red fluorescent protein and the intracellular location of the hybrid protein is determined. In another analytical method, a nucleic acid comprises a heterologous (i.e., non-*Discosoma* RFP) regulatory element operatively linked to the nucleotide sequence encoding the yeast-enhanced red fluorescent protein, such as, for example, a *C. albicans* regulatory element. The activity of the regulatory element in response to a stimulus can be analyzed by detecting a change in fluorescence. In certain non-limiting embodiments, the stimulus is an environmental stimulus, or the stimulus is a modulation of a protein that affects expression from the regulatory element.

In another application, the analysis method further comprises evaluating expression of a second fluorescent protein which is excited or fluoresces at a wavelength that is distinguishable from the red fluorescent protein. In yet further, applications, the analysis method may be performed wherein the second fluorescent is a variant red fluorescent protein, or wherein the second fluorescent protein is green fluorescent protein from *Aequorea victoria* or a variant thereof.

In another embodiment, the invention provides a method of determining the stability of an extrachromosomal plasmid in a *Candida albicans* cell comprises introducing into the cell an extrachromosomal plasmid comprising a nucleic acid that expresses a yeast-enhanced red fluorescent protein and detecting the presence of the yeast-enhanced red fluorescent protein in daughters of the cell.

In further embodiments, the invention provides a method of determining plasmid stability in a *C. albicans* cell, wherein the presence of the yeast-enhanced red fluorescent protein is detected by fluorescence, or by colony color. In one such embodiment, the stability of the extrachromosomal plasmid is determined by observing colony sectoring.

The invention provides a method of identifying a substance as a factor that modulates maintenance of an extrachromosomal plasmid in *C. albicans* is carried out, which comprises: a) providing a *C. albicans* cell which contains an extrachromosomal plasmid that expresses a yeast-enhanced red fluorescent protein; b) introducing the test substance into the cell; and c) monitoring maintenance of the plasmid by observing expression of the yeast-enhanced red fluorescent protein.

In a further application, the invention provides a method of identifying a test substance that modulates a regulatory element of *C. albicans*, which comprises: a) providing a *C. albicans* cell which contains a nucleic acid comprising the regulatory element operatively linked to a nucleotide sequence that encodes a yeast-enhanced red fluorescent protein; b) contacting the *C. albicans* cell with the test substance; and c) determining whether expression of the yeast-enhanced red fluorescent protein is modulated. In further embodiments, the test substance is introduced into the environment of the cell, or the test substance is introduced into the cell or contacted with the cell.

The invention also provides a means for studying the pathology of yeast. In one embodiment, the yeast enhanced RFP is used as a reporter of gene expression, for example, to detect transcriptional activity of a gene of a pathogen that is modulated by interaction with host animal tissue. In another embodiment, the yeast enhanced RFP is useful to detect the presence of the pathogen in host animal tissue.

The invention provides a kit comprising a nucleic acid for expressing a yeast-enhanced red fluorescent protein. In one embodiment, the kit comprises a host, such as a *C. albicans* or *S. cerevisiae*. Typically, the kit contains instructions for use in the methods set forth herein.

DESCRIPTION OF THE FIGURES

FIG. 1 shows expression of yEmRFP in *C. albicans*. A. Immunofluorescence of yEmRFP in *C. albicans*. *C. albicans* cells (BWP17) expressing yEmRFP from a *C. albicans* ARS/URA3 plasmid (pCaADH1-yEmRFP, see below) were grown in YPAD (upper panel) at 30° C. or diluted to 0.4 OD A600 in YPAD+20% bovine calf serum and grown at 37° C. for hyphal induction (lower panel) and directly viewed by fluorescence microscopy, using an RFP-specific filter set. B. Sectoring assay of yEmRFPexpressing *C. albicans* cells.

FIG. 2 shows expression of yEmRFP resulting in purple colony color in *S. cerevisiae*. A. ADE2 or ade2 (W303-1A) *S. cerevisiae* cells were transformed with a URA3-marked 2μ plasmid containing TDH3-promoter driven yEmRFP (yEpGAP-Cherry) or the vector (yEpGAP), plated on SD(-Ura) plates and incubated for 3 days at 30°. B. Random spore analysis on nonselective media. An ADE2/ade2 ura3/ura3 strain containing the 2μ plasmid-borne yEmRFP (yEpGAP-Cherry) was sporulated in 1% potassium acetate. Yeast spores were enriched and plated on non-selective medium for 5 days to allow ade2-dependent red color to develop. Genotypes of representative colonies are shown.

FIG. 5 shows a comparison of the DNA and protein sequence of human and yeast-optimized mRFP (yEmRFP). A yeast codon-optimized mRFP gene (GenBank accession # EU262302; SEQ ID NO:1) was synthesized (Blue Heron, Bothell, Wash.) based on the protein sequence of the mCherry mRFP variant (Shaner et al., Nature Biotech. 22: 1567-1572 (2004); GenBank Acc. No. AY678264; SEQ ID. NO. 11).

FIG. 6 compares codon usage of mRFP (mCherry) and the corresponding yEmRFP.

DETAILED DESCRIPTION

Figure 3:
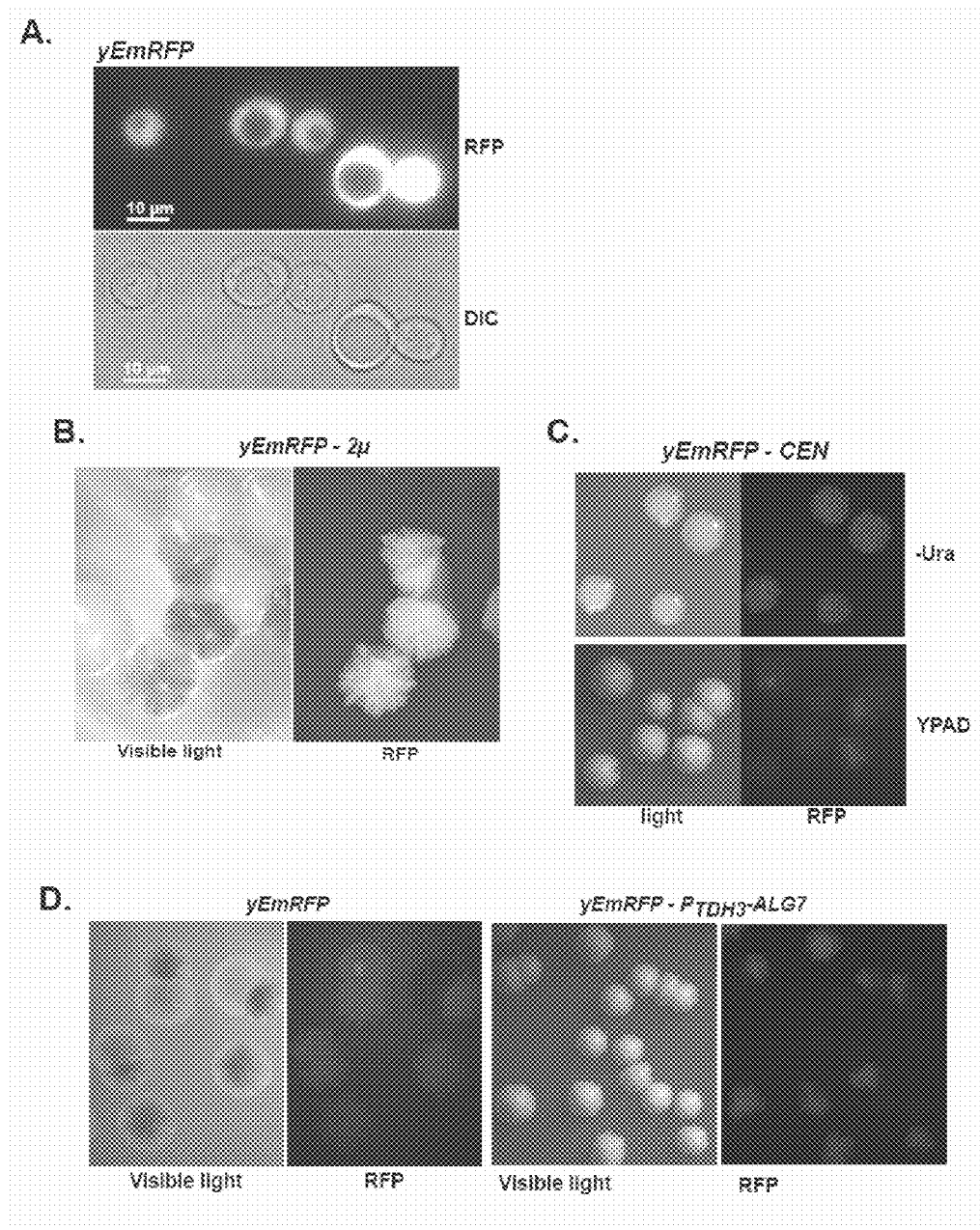
FIG. 3 depicts correlation of cell color and fluorescence phenotypes. A. Immunofluorescence of cells (SEY6210) harboring the 2μ yEmRFP plasmid (yEpGAP-Cherry) grown overnight in medium lacking uracil to select for plasmid maintenance. Cells were directly viewed by fluorescence microscopy, using an RFP-specific filter set. B. Visual and fluorescent assay monitoring the maintenance of a yEmRFP-containing plasmid in colonies. Purple/white sectored colonies were viewed by light microscopy (left panel) or fluorescence (right panel) using a Leica MZFLIII fluorescence stereomicroscope. C. Sectoring assay of *S. cerevisiae* cells expressing yEmRFP on a low copy, CEN plasmid. Colonies were analyzed for plasmid loss by a sectoring assay using fluorescence microscopy as described above (panel B). D. Changes in yEmRFP plasmid-dependent colony color and sectoring phenotypes can be induced by linkage to a gene whose over expression is deleterious. Colony color and fluorescence were monitored visually and by fluorescence as described in panel B.

The invention provides a novel nucleic acids encoding red fluorescent proteins (RFPs) expressible in *Candida albicans*. In certain embodiments, the RFPs impart a particularly useful color phenotype when expressed in *C. albicans* and other yeast (e.g., *Saccharomyces cerevisiae*). The present invention also provides a non-limiting selection of uses in genetic, physiological, and pathological studies of *C. albicans* and other yeast. According to the invention, red fluorescent protein means the red fluorescent protein of *Discosoma* (which form tetramers) and variants of that protein that form monomers or dimers and/or vary in fluorescence and color properties. Preferred red fluorescent proteins also do not aggregate (i.e., are monomeric). Non-limiting examples of mRFPs having varying fluoresence characteristics include mCherry, mBanana, mStrawberry, mOrange, etc. (See, e.g., Shaner et al., Improved monomeric red, orange and yellow fluorescent proteins derived from *Discosoma* sp. red fluorescent protein. Nature Biotech 22: 1567-1572 (2004)). The family of red fluorescent proteins encompassed by the invention have amino acid sequences that are at least about 70%, at least about 80%, at least about 90%, or at least about 95% homologous to the monomeric (mCherry) variant of the red fluorescent protein of *Discosoma* having SEQ ID NO:2. RFP variants also include those that have been modified at their N-terminal and/or C-terminal ends to minimize loss of fluorescence intensity when incorporated into a fusion protein.

The RFPs of the invention can be used in other yeasts, as well. Traditionally, species of yeasts that were thought to be asexual were given the genus name *Candida*. Many of these species are pathogenic as well, and appear very similar visually and microscopically. However, this system breaks down when molecular phylogenetics is applied, and certain *Candida* species, such as *Candida glabrata*, are found within the *Saccharomyces* clade, whereas others (i.e., *C. albicans*) are not.

It has been discovered that the previous inability to express mRFP in *C. albicans*, as well as the poor expression of mRFP in other yeasts, is attributable to incompatible codon usage since synonymous codons of yeast are biased toward an A or T at the third position. To enhance mRFP expression in *S. cerevisiae*, as well as other AT-rich yeast and fungi, mutations were introduced in the mCherry mRFP variant (Shaner et al., Improved monomeric red, orange and yellow fluorescent proteins derived from *Discosoma* sp. red fluorescent protein. Nature Biotech 22: 1567-1572 (2004)) to maximize the codon bias towards the more frequent AT-rich codons. 98% of mCherry codons contain a C or G at the third position so in total, 218 out of 237 codons were altered to produce a yeast-enhanced mRFP (yEmRFP) (FIG. 5, FIG. 6).

Efficient expression of the RFPs of the invention in *C. albicans* represents a significant advance in the art. The present invention can be used as a genetic tool to investigate a variety of questions in *C. albicans*, such as factors that contribute to extrachromosomal plasmid maintenance in *C. albicans*, protein localization, gene expression, etc. In particular, the present invention provides yEmRFPs useful in two (or more) color fluorescence assays in *C. albicans*, which were previously not available to researchers. Using two or more color markers researchers can discriminate between many cell types, multiple transcriptional activities or monitor multiple fusion proteins (see e.g. Wei Wen Su, Fluorescent proteins as tools to aid protein production, Microbial Cell Factories 4:12 (2005)). Other yeast enhanced mRFP variants expressible in *C. albicans* include, but are not limited to mStrawberry, mTangerine, mOrange, mBanana, mHoneydew (Shaner et al. (2004) and mBlueberry2 (Ai, H-w. et al., Exploration of New Chromophore Structure Leads to Identification of Improved Blue Fluorescent Proteins, Biochemistry 46:5904 (2007)).

Unexpectedly, certain yEmRFPs are chromoproteins, which when expressed in yeast cells, provide a remarkable visual color indicator under natural light. In *S. cerevisiae* cells that express SEQ ID NO:1 from a high copy vector, a vivid purple color is observed (FIG. 2A). A visible, though less intense, color phenotype is also observed in *C. albicans* (FIG. 1B). These results were surprising because an RFP-dependent color phenotype in the visual range has not been reported.

Thus, according to the invention, yEmRFPs can be detected by fluorescence or by color under natural light. In assays using a second reporter protein, such as green fluorescent protein (GFP) or a GFP variant, in addition to a yEmRFP, the yEmRFP can be detected either by fluorescence at its characteristic wavelength or by colony color, while the second reporter is detected by fluorescence at a different wavelength. GFP is the green fluorescent protein from *Aequorea victoria*. Variants of GFP are mutants that have excitation and/or emission peaks shifted to other wavelengths. These include versions of GFP with blue, cyan, and yellow fluoresecence (BFP, CFP, and YFP respectively).

Previously, the only reliable color phenotype used in yeast was the red/brown color which develops in ade2 mutant yeast as a result of a block in adenine production. Transformation of an ade2 mutant cell with a vector expressing a complementary wild type ADE2 gene is indicated by a normal white phenotype. Accordingly, the ade2 color phenotype has been used, for example, to monitor transformation of yeast cells with genes linked to ADE2, to monitor stability of yeast chromosomes and plasmids (Hieter et al., Mitotic stability of yeast chromosomes: a colony color assay that measures nondisjunction and chromosome loss. Cell 40: 381-392 (1985); Koshland et al., Genetic analysis of the mitotic transmission of minichromosomes. Cell 40: 393-403 (1985)), and to identify numerous types of genetic interactions, including synthetic lethality and dosage suppression (see e.g. Bender et al., Use of a screen for synthetic lethal and multicopy suppressee mutants to identify two new genes involved in morphogenesis in *Saccharomyces cerevisiae*. Mol. Cell. Biol. 11: 1295-1305 (1991)).

The present invention also provides an easy to use visual indicator which can be similarly applied, but has several important advantages over ade2. First, cells expressing this protein can be identified both visually by their color and also by very sensitive fluorescence-based assays. Second, color development occurs more rapidly than ade2-induced red. For example, purple color in cells expressing the mCherry variety of yEmRFP (SEQ ID NO:1) can be identified after an overnight incubation, rather than after 3-5 days, as is required for ade2-induced red. Third, unlike the ade2 mutation, which must be engineered into the chromosome, this color is plasmid dependent and dominant, and therefore can be introduced into any yeast strain background. This provides a powerful new genetic tool for studies in *S. cerevisiae* and other yeast and fungi in which it can be expressed. Nevertheless, even when a yEmRFP gene of the invention is chromosomally integrated, a distinctive color and fluorescence is observed.

As mentioned, in one embodiment, the fluorescent protein is the mCherry variant of RFP. In another embodiment, the fluorescent protein of the invention has an amino acid sequences which is at least about 70%, or at least about 80%, or at least about 90%, or at least about 95% identical to the mCherry RFP variant, or at least 80%, or at least about 90%, or at least about 95% homologous to the mCherry RFP variant, as determined by the FASTA search method in accordance with Pearson and Lipman (*Proc. Natl. Acad. Sci. USA* 85: 2444-8 (1998)). The mCherry variant is an example of an RFP which has been modified by incorporation of at its N- and C-terminus of several amino acids from green fluorescent protein. Consequently, sequence similarity to mCherry should be determined only over the amino acid positions that correspond to mRFP (Campbell et al., *Proc. Natl. Acad. Sci. USA* 99: 7877-82 (2002), i.e., SEQ ID NO:2 from amino acid 12 to amino acid 230. Non-limiting examples of nucleic acids of the invention and proteins express therefrom, are provided in Table 1.

TABLE 1

SEQ ID NOS for nucleic acid and amino acid sequences
of yeast-enhanced monomeric red fluorescent proteins

| fluorescent protein designation | yeast-enhanced nucleic acid | amino acid |
|---|---|---|
| mCherry | 1 | 2 |
| mStrawberry | 3 | 4 |
| mOrange | 5 | 6 |
| mBanana | 7 | 8 |
| mBlueberry2 | 9 | 10 |

Yeast-enhanced RFPs of the invention include those encoded by nucleic acids that specifically hybridize (or specifically bind) under stringent hybridization conditions to SEQ ID NO:1, SEQ ID NO:3, SEQ ID NO:5, SEQ ID NO:7, and SEQ ID NO:9. Hybridization under stringent conditions refers to conditions under which a probe will hybridize preferentially to its target subsequence, and to a lesser extent to, or not at all to, other sequences. It also will be understood that stringent hybridization and stringent hybridization wash conditions in the context of nucleic acid hybridization experiments such as southern and northern hybridizations are sequence dependent, and are different under different environmental parameters. It is well known in the art to adjust hybridization and wash solution contents and temperatures such that stringent hybridization conditions are obtained. Stringency depends on such parameters as the size and nucleotide content of the probe being utilized. See Sambrook et al., 1989, Molecular Cloning—A Laboratory Manual (2nd ed.) Vol. 1-3, Cold Spring Harbor Laboratory, Cold Spring Harbor Press, NY, and other sources for general descriptions and examples. Another guide to the hybridization of nucleic acids is found in Tijssen, 1993, Laboratory Techniques in Biochemistry and Molecular Biology—Hybridization with Nucleic Acid Probes, part I, chapter 2, Overview of principles of hybridization and the strategy of nucleic acid probe assays, Elsevier, N.Y.

Preferred stringent conditions are those that allow a probe to hybridize to a sequence that is more than about 90% complementary to the probe and not to a sequence that is less than about 70% complementary. Generally, highly stringent hybridization and wash conditions are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Very stringent conditions are selected to be equal to the $T_m$ for a particular probe.

An example of stringent hybridization conditions for hybridization of complementary nucleic acids which have more than 100 complementary residues on a filter in a Southern or northern blot is 50% formamide with 1 mg of heparin at 42° C., with the hybridization being carried out overnight. An example of highly stringent wash conditions is 0.15 M NaCl at 72° C. for about 15 minutes. An example of stringent wash conditions is a 0.2 times SSC wash at 65° C. for 15 minutes (see, Sambrook et al., 1989). Often, a high stringency wash is preceded by a low stringency wash to remove background probe signal. An example of a medium stringency wash for a duplex of, e.g., more than 100 nucleotides, is 1 times SSC at 45° C. for 15 minutes. An example of a low stringency wash for a duplex of, e.g., more than 100 nucleotides, is 4-6 times SSC at 40° C. for 15 minutes. In general, a signal to noise ratio that is two times (or higher) that observed for an unrelated probe in the particular hybridization assay indicates detection of a specific hybridization.

As set forth above, yeast-enhanced RFPs of the invention include proteins that are similar, but not identical to SEQ ID NO:2. It is to be expected that a variety of amino acid substitutions can be made in RFPs of the invention that are specifically disclosed in Table 1. Current technology allows one of skill in the art to easily make sequence variations by design or at random, and test their results. Conservative amino acid substitution is defined as a change in the amino acid composition by way of changing one or a few amino acids of a peptide, polypeptide or protein, or fragment thereof. The substitution is of amino acids with generally similar properties (e.g., acidic, basic, aromatic, size, positively or negatively charged, polarity, non-polarity) such that the substitutions do not substantially alter peptide, polypeptide or protein characteristics (e.g., charge, isoelectric point, affinity, avidity, conformation, and solubility) or activity. Typical substitutions that may be performed for such conservative amino acid substitution may be among the groups of amino acids as follows:

glycine (G), alanine (A), valine (V), leucine (L) and isoleucine (I);
aspartic acid (D) and glutamic acid (E);
alanine (A), serine (S) and threonine (T);
histidine (H), lysine (K) and arginine (R):
asparagine (N) and glutamine (Q);
phenylalanine (F), tyrosine (Y) and tryptophan (W)

One of ordinary skill in the art would understand that not all residue positions within a RFP will tolerate a substitution, conservative or otherwise. For example, the residues that compose the chromophore will not generally tolerate substitutions. However, one of skill in the art is able to make substitutions to modify the chromophore, such that it retains fluorescence and/or color, but with different absorption and/or emission characteristics. See, e.g., Shaner et al. (2004). The three dimensional structure of RFP has been determined, and provides guidance in this respect. Also, one of skill in the art would understand how to generate and screen libraries of RFP mutants for useful variants.

According to the invention, a protein encoding sequence is optimized for expression in *C. albicans* and other yeasts by replacing codons that are used infrequently in a host organism with codons that encode the same amino acid, but are used more frequently. Codon usage tables, which have been tabulated from GenBank data for a large variety of organisms, are available from, for example, Kazusa DNA Research Institute (Japan) and European Bioinformatics Institute, (Cambridge, UK) and are readily accessible online. When designing a nucleotide sequence enhanced for expression in a particular host cell, it will generally be desirable to select codons that are most frequently used that host. Certain yeast-enhanced RFP encoding nucleotide sequences disclosed herein (SEQ ID NOS:1, 3, 5, 7, 9) utilize the highest frequency codons at every amino acid position. However, protein expression in yeast, including C. albicans, can be significantly enhanced even without optimizing every codon, and without choosing the best codon at every position. Accordingly, codons should be chosen for an amino acid that are used with a frequency of at least about 30% in the host. Further, at least 50% of codons that can be optimized, more preferably 75% of codons that can be optimized, should be optimized, and codons with frequencies of less that about 25% should be avoided. Also, the CUG codon, which encodes leucine in C. albicans, as opposed to serine in other organisms, should be avoided.

As mentioned, the invention provides nucleic acids that encode yeast-enhanced red fluorescent proteins that are expressible in C. albicans. As used herein, the term "expressible" refers to that level of protein expression that gives rise to detectable color or fluorescence. It will be appreciated that the color and/or fluorescence intensity in cells or colonies in which the yEmRFP is expressed will be affected by gene copy number and promoter strength. For example, expression from a multicopy plasmid with a suitable strong promoter results in expression of an intense color or fluorescence phenotype, whereas the same yEmRFP construct, present in a few copies, in a vector or integrated into a host chromosome, would yield paler color or weaker fluorescence. It will also be appreciated that RFPs that are not yeast enhanced according to the invention may be observable in C. albicans or other yeasts by fluorescence or color under selected circumstances, for example through the use of particularly sensitive detection equipment, by using a sufficiently strong promoter to express the protein, by providing the nucleic acid in a sufficiently high copy number, or a combination of the foregoing, though expression is insufficient to be useful for the types of assays in which such fluorescent proteins are typically used. Compared to RFPs that are not yeast enhanced, and under the same expression conditions (i.e., promoter and gene copy number), the color or fluorescence conferred by yeast-enhanced RFPs of the invention is at least double, or quadruple, or 10×, or 20×, or 50×, or greater. Color or fluorescence can be detected visually, or determined with, e.g., a fluorimeter or spectrophotometer.

Monitoring the fate of a fungal pathogen during the course of an infection is essential for understanding how virulence factors affect fungal adhesion, tissue invasion, colonization, and morbidity. There are several model systems that are currently used to examine how mutations in different genes of pathogens such as C. albicans genes affect pathogenesis. These systems include, for example, in vivo mouse and in vitro macrophage models of infection, in which the presence of C. albicans is assayed by microscopic examination of stained sections of infected tissue or cells. These techniques are laborious, time consuming, and costly.

An RFP of the invention is useful for monitoring pathogenesis in a host. Notably, while providing a distinct color marker, expression of a yEmRFP of the invention has no apparent effect on the viability of the pathogen when it is expressed. Accordingly, the RFP provides a useful marker for tracking infection of animal tissue and for determining whether a test compound or treatment regime is effective in limiting or blocking the infection.

Figure 8:
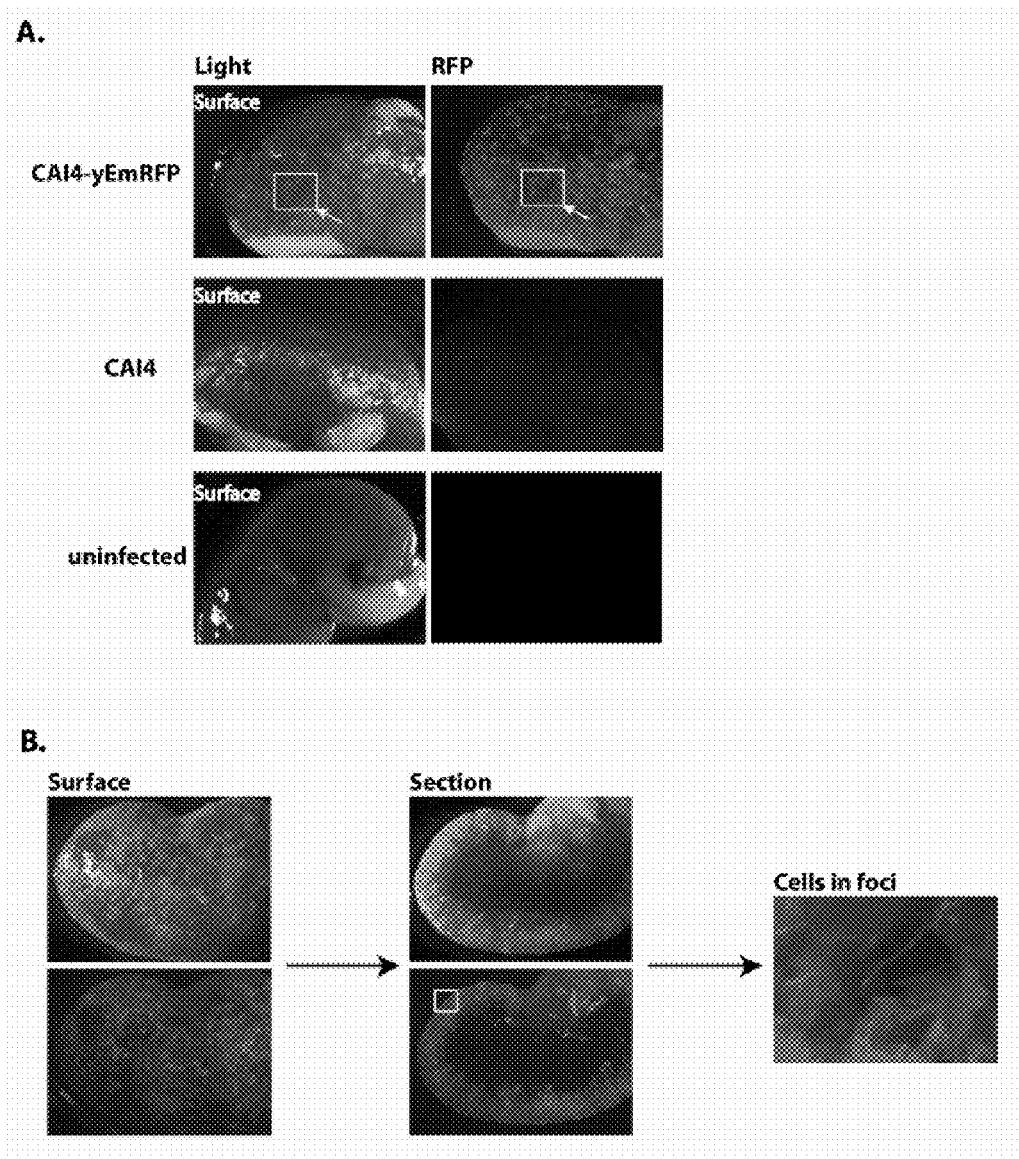
FIG. 8 shows kidneys from uninfected mice or mice infected with non-fluorescent *C. albicans* strain CAI4 or an isogenic fluorescent strain (SKY40). After imaging the surface of the kidney with light or RFP-specific filters, the kidney was sliced longitudinally in half to image its interior.
Figure 9:
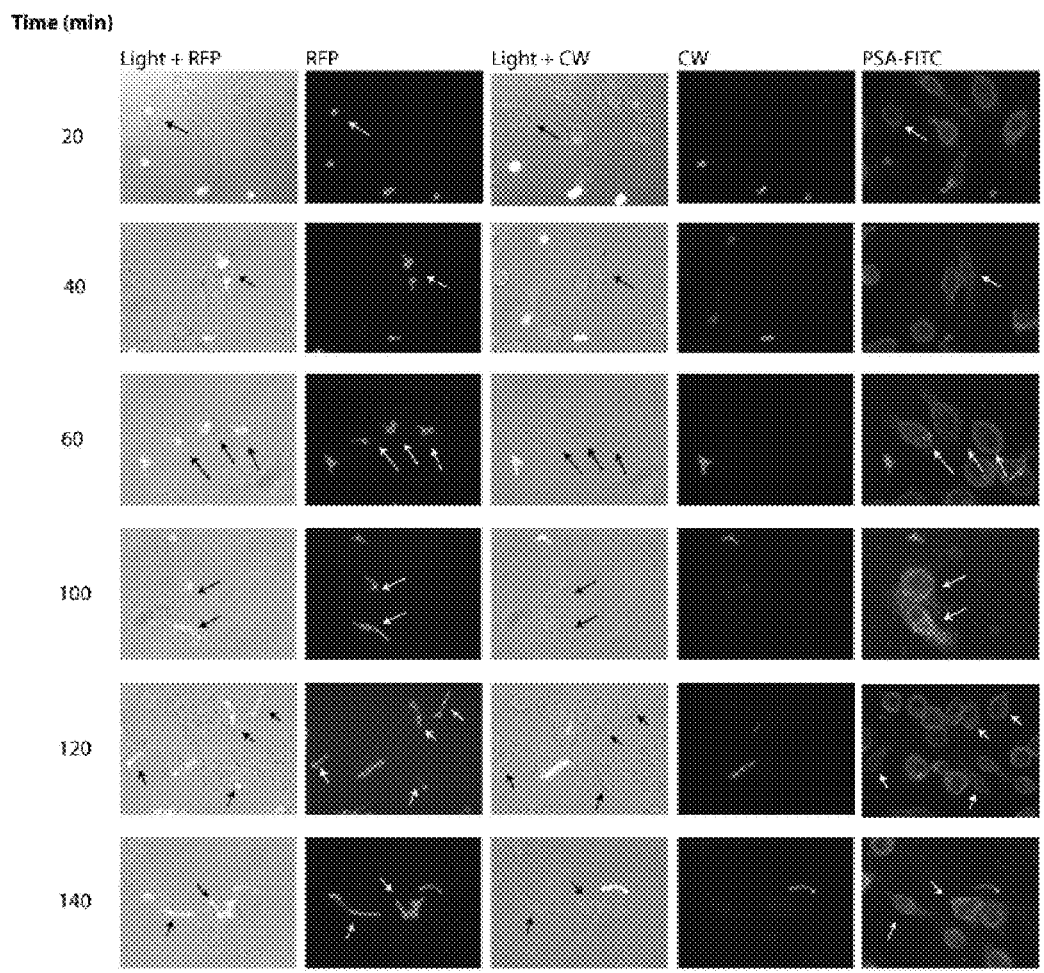
FIG. 9 depicts phagocytosis of fluorescent *C. albicans* fungal cells by macrophages. Fluorescent *C. albicans* cells were added to macrophages for 5-10 minutes. Macrophages (with adherent or internalized yeast cells) were stained and imaged at various times post-infection. Calcofluor white (CW) and PSA-FITC labels adherent, but not internalized, yeast cells.
Figure 10:
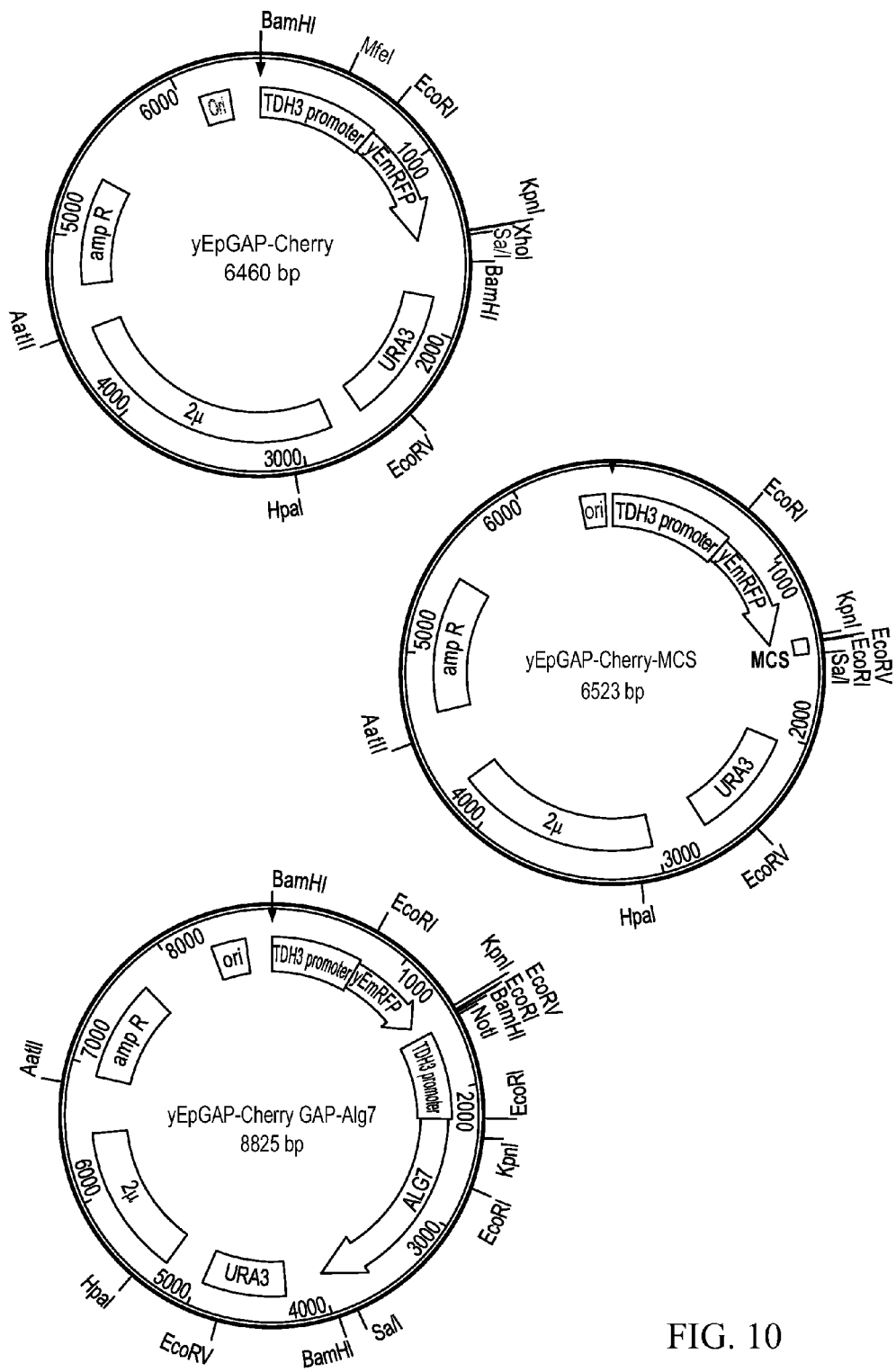
FIG. 10 depicts gene vectors for expression of yeast-enhanced red fluorescent proteins according to the invention.

C. albicans and other related yeasts are able to survive and proliferate in and on a range of different tissues in a variety of hosts. Infections can be local, including primarily superficial infection of mucosal tissue and skin, but organs, not limited to kidneys, brain, liver, and spleen, are also sites of colonization. Systemic infection is particularly problematic following invasive surgery, such as, but not limited to gastrointestinal surgery, and in patients treated with immunosuppressive drugs. From the bloodstream, cells may infect almost all organs. The invention provides assays for tracking pathogens such as C. albicans, both in vivo, such as in infected mice or other test subjects, and in vitro, for example in isolated tissue or cells, including phagocytosis by macrophages. Particular assays disclosed or exemplified herein take advantage of constitutive expression in C. albicans of codon-optimized red fluorescent protein (yEmRFP), whose production results in brilliantly fluorescent, morphologically pink fungal cells. Several such C. albicans strains (SKY 38, SKY39, SKY40) have been constructed that contain multiple integrated copies of yEmRFP driven by the ADH1 promoter. The pink colony morphology and fluorescence phenotype is genetically stable and has no apparent affect on growth, hyphal formation, or virulence properties. Organisms expressing a yeast-enhanced red fluorescent protein of the invention are otherwise physiologically normal. Consequently, the red fluorescent proteins can be used for observation of fungal infection of tissues or cells. Non-limiting examples of mouse and macrophage models of fungal infection are exemplified herein. For instance, fungal burden in organs can be monitored and quantitated by simple fluorescence microscopy without any manipulation of cells (FIG. 8), and cellular uptake of fluorescent pathogens (e.g. by macrophages) can be observed (FIG. 9). Such assays and strains provide the ability to quickly assay the effect of mutations and/or chemicals that influence fungal pathogenesis.

Yeast-enhanced RFPs of the present invention are also suitable for use as markers for transformation. Often, a gene of interest does not produce an easily distinguishable phenotype in cells expressing that gene. Thus, such a gene is usually inserted into a vector that contains a marker gene. The therapeutic gene and the marker gene are placed in the vector under the control of regulatory sequences functional in yeast, and introduced into C. albicans (or other yeast) cells of interest. Subsequently, the transformed cells containing the vector are screened or selected according to the phenotype determined by the marker gene. In C. albicans and S. cerevisiae, the distinctive color phenotype displayed by cells expressing yEmRFP of the present invention is particularly useful for identifying and isolating colonies of cells transformed with plasmids expressing the yeast-enhanced RFP and carrying a linked gene of interest. The use of yeast-enhanced RFP for screening obviates the need to grow the yeast or C. albicans cells of interest in the presence of drugs that might be used with other markers. Cells transformed with a vector containing yEmRFP and the gene of scientific interest can be recognized by the particular excitation and fluorescence wavelength (which will vary according to the yEmRFP that is used) and sorted by FACS.

The bright color conferred by yEmRFP provides a useful marker for monitoring genetic events that influence plasmid uptake, maintenance, and stability. Cells that maintain the yEmRFP plasmid can be reliably distinguished from those that lose it with high sensitivity, by either a visual or fluorescence assay. For example, the mechanism of plasmid stability in C. albicans is not understood. In C. albicans, ARS-containing plasmids are extremely unstable. There is wide cell-to-cell variation in copy number, and the plasmids may be integrated into the genome, or lost in the absence of selection. By enabling expression of yeast-enhanced RFP's in *C. albicans*, the present invention provides means by which the extrachromosomal stability of different plasmids may be tested in *C. albicans*. For example, an ARS-containing plasmid library can be constructed containing *C. albicans* chromosomal sequences and a gene that expresses a yeast-enhanced RFP in order to identify chromosomal elements that contribute to plasmid stability. The library is then transformed into *C. albicans*, and the stability of the extrachromosomal element is monitored by observing, for example, uniformity of fluorescence in individual cells or colony sectoring.

Similarly, when linked to a gene of interest, the RFPs can be used to measure changes in the stability of the vector which result from expression of the linked gene. For example, an RFP-containing vector may be observed to be less stable when carrying or expressing a nucleotide sequence whose presence is detrimental to a host cell. Further, such a vector can be used to identify genetic or chemical interactions which affect the toxicity (e.g., which is observed as instability) of the linked nucleotide sequence.

Yeast-enhanced RFPs of the present invention can also used to select cell lines in which expression vectors have integrated at a chromosomal location giving very high expression of yeast-enhanced RFP and of a gene of interest. For example, an expression vector containing a yEmRFP and a gene of interest is transformed into yeast or *C. albicans* cells along with a vector expressing a gene of interest. Screening for cells that fluoresce relatively brightly will yield cells with relatively high levels of expression of the gene of interest.

Yeast-enhanced RFPs of the present invention can be further used to identify promoters and other regulatory elements, including but not limited to enhancers and negative regulatory elements (and consequently genes normally driven by those promoters) that regulate gene expression in response to a specific stimulus. For example, a library is created using nucleic acids placed upstream of a sequence encoding a yEmRFP of the present invention, and the library is transformed into the host organism. The upstream sequences contain promoter sequences and other regulatory elements of the organism of interest. The organism is then subjected to a stimulus of interest and cells that respond with changes in color or fluorescence are identified. In an embodiment of the invention, the stimulus is an "environmental" stimulus, such as one associated with infection. Non-limiting examples of such stimuli include contact with or adhesion to host tissues (e.g., human, mouse, or other susceptible host), and changes in carbon dioxide and oxygen concentrations. Similarly, test substances can be screened to identify those that block or inhibit such responses.

One way to identify such cells is by FACS. For example, sequential sortings can be used to enrich a fraction of cells that expresses increased RFP levels in the presence of a stimulus and decreased levels in its absence. In one embodiment, such a procedure is performed to monitor responses to stimuli such as those encountered by pathogenic organisms during infection.

One particular advantage of the visible RFP color phenotype is its stability under natural light. RFPs, when stimulated to fluoresce, undergo photobleaching at various rates. In contrast, the color phenotype conferred by an RFP of the invention is stable. Thus, the expression of a gene in *C. albicans* or other yeast, particularly over an extended time period, can be determined using an assay that detects color intensity. For example, colony color can be visualized by comparison to a standard color reference, or a calorimetric determination can be made. Further, changes in color intensity can be used to detect changes in gene expression in response to, for example, interactions between a pathogen and its host.

For the study of protein localization, fusion of a yeast-enhanced RFP of the present invention and a gene encoding a protein of interest encoding for a cellular protein, and subsequent expression of the hybrid protein, results in localization of the fluorescent fusion protein to the normal intracellular location of the protein of interest. The location of the hybrid protein can be determined, for example, using fluorescence microscopy. The hybrid protein yields information not only on the cellular location of the protein, but also changes in location or distribution of the protein. Accordingly, hybrid RFPs of the invention may be used to examine protein trafficking, responses of proteins to factors in the environment, correlation of protein translocation with stages in the life cycle of the cell, and the like. Vectors that can be used for fusing a protein of interest to the N-terminus or the C-terminus of yEmRFP are producible by methods known to one of ordinary skill in the art.

Dual color fluorescent analysis in *C. albicans* is also enabled by the present invention. For example, a yEmRFP of the present invention, such as the mCherry variant, and a first gene of interest encoding for a cellular protein are concatenated and expressed together as for a normal mono-color fluorescent analysis. However, in addition to the chosen yEmRFP, another yEmRFP, for example the mBlueberry2 variant, is concatenated with a second gene of interest so that expression is simultaneous with that of the mCherry variant and the first gene of interest. By visualizing fluorescence within the host cells at the appropriate wavelengths, and combining the resulting images by means commonly known to those of ordinary skill in the art, a dual color image displaying chromosomal location for both proteins is obtained. The secondary fluorescent protein may also be a green fluorescent protein (GFP) or a color variant thereof. The present invention can also be used to carry out multi-color fluorescent analysis using more than two RFP's of differing fluorescence.

The invention provides acceptor-donor pairs of fluorescent proteins for use in Fluorescence Resonance Energy Transfer (Förster Resonance Energy Transfer; FRET) experiments. FRET is a distance-dependent non-radiative energy transfer between an excited donor and an acceptor. The phenomenon can be used to investigate intermolecular and intramolecular protein-protein interactions. For example, when there is an interaction between two proteins tagged with two different fluorochromes, as the distance between the fluorochromes decreases, non-radiative energy transfer increases. In the case of donor and acceptor fluorescent proteins, when the donor is excited, a portion of its energy is transferred in a non-radiative manner to the acceptor protein without photon emission, and the excited acceptor protein fluoresces in turn. The functionality of fluorescent protein donor-acceptor pairs depends on several characteristics, such as overlap of donor emission wavelength and acceptor excitation wavelengths, and the degree to which emissions of the donor and acceptor are distinguishable. A variety of useful donor-acceptor pairs are known in the art, several of which incorporate GFP or GFP variants as donors and RFP or RFP variants as acceptors. One common combination is GFP/RFP. Another is GFP/mCherry which has desirable emission and photostability characteristics. mOrange can also be paried with GFP, or more preferably with a GFP variant designated T-sapphire. Accordingly, the yeast-enhanced mRFP variants of the invention provide FRET acceptors for use in *C. albicans*.

The possible applications of the present invention described herein are merely representative and are non-limiting.

A "fluorescent" label may be detected by exciting the fluorochrome with the appropriate wavelength of light and detecting the resulting fluorescence. The fluorescence may be detected visually, or by the use of electronic detectors such as charge coupled devices (CCDs) or photomultipliers and the like. FACS analysis and fluorescence microscopy are preferred methods of detection when the label is in a cell.

A "vector" is any vehicle used to transfer foreign genetic material to another cell. The vector may be a plasmid, phage or cosmid, to which another DNA segment may be attached so as to bring about the replication of the attached segment. The invention includes vectors that replicate autonomously in C. albicans or S. cerevisiae or other yeasts, as well as vectors that undergo stable chromosomal integration.

Any suitable expression vector can be used. The expression vectors useful in the present invention contain at least one expression control sequence that is operatively linked to the DNA sequence or fragment to be expressed. The control sequence is inserted in the vector in order to control and to regulate the expression of the cloned DNA sequence. Examples of useful expression control sequences include the ADH1 promoters of C. albicans and S. cerevisiae, the glycolytic promoters of yeast, e.g., the promoter for 3-phosphoglycerate kinase, the promoters of yeast acid phosphatase, e.g., Pho5, the promoters of the yeast alpha-mating factors, Examples that can be useful for cloning and expression in E. coli are the lac system, the trp system, the tac system, the trc system, major operator and promoter regions of phage lambda, and the control region of fd coat protein of the f1 phage. Further examples of useful vectors are exemplified elsewhere herein.

The term "host cell" refers to any biological cell or organism that can be transformed with nucleic acid sequences of the present invention. The present invention provides recombinant host cells containing the expression vectors previously described. Host cells include those considered in the art to be generally useful art of yeast genetics. Useful strains of C. albicans and S. cerevisiae are well known and include those exemplified herein. One of skill in the art knows how to choose or create fungal cells appropriate for any particular application. Useful prokaryotic hosts for manipulating nucleic acids include, for example, E. coli, such as E. coli SG-936, E. coli HB 101, E. coli W3110, E. coli X1776, E. coli X2282, E. coli DHI, and E. coli MRC1.

Transformed host cells are cultured by methods known in the art in a liquid medium containing assimilable sources of carbon, e.g. carbohydrates such as glucose or lactose, nitrogen, e.g. amino acids, peptides, proteins or their degradation products such as peptones, ammonium salts or the like, and inorganic salts, e.g. sulfates, phosphates and/or carbonates of sodium, potassium, magnesium and calcium. The medium furthermore contains, for example, growth-promoting substances, such as trace elements, for example iron, zinc, manganese and the like.

Also provided by the invention are kits for use in, for example, one or more of the above described applications. The kits contain elements for expressing a yEmRFP of the invention, either alone or linked to a protein or polypeptide of interest, and typically include a nucleic acid encoding a yEmRFP. The nucleic acid may be contained in a vector suitable for expression in a yeast, particularly C. albicans or S. cerevisiae. The vector may be designed for insertion of expression control sequences, such as constitutive or regulated promoters and enhancers active in C. albicans and/or S. cerevisiae. Alternatively, the vector may be designed for insertion of nucleotides that encode proteins or protein fragments such that hybrid proteins comprising a yEmRFP are expressed. The kit components may be lyophilized or present in a buffered solution, typically in a suitable container. In another embodiment, a kit of the invention contains a yeast strain, such as a strain of C. albicans or S. cerevisiae, that expresses a yEmRFP. In an embodiment of the invention, the yeast strain is a pathological yeast strain. In addition to the biological components, kits of the invention will typically include instructions for use of the packaged materials.

Throughout this application, various publications, reference texts, textbooks, technical manuals, patents, and patent applications have been referred to. The teachings and disclosures of these publications, patents, patent applications and other documents in their entireties are hereby incorporated by reference into this application to more fully describe the state of the art to which the present invention pertains.

EXAMPLES

It is to be understood and expected that variations in the principles of invention herein disclosed may be made by one skilled in the art and it is intended that such modifications are to be included within the scope of the present invention. The following examples only illustrate particular ways to use the novel red fluorescent protein of the invention, and should not be construed to limit the invention.

Example 1

Expression and Stable Integration of Plasmids in C. Albicans

Mutations were introduced, by means known to one of ordinary skill in the art, to the mCherry mRFP variant to maximize the codon bias towards the more frequent AT-rich codons. 218 out of 237 codons were altered to produce a yeast-enhanced mRFP (yEmRFP) (SEQ ID NO:1). A CaADH1 promoter-driven yEmRFP was cloned in a CaURA3-marked plasmid containing an autonomously replicating sequence (ARS). C. albicans cells (BWP17) (Wilson et al., Rapid hypothesis testing with Candida albicans through gene disruption with short homology regions. J. Bacteriol. 181: 1868-1874 (1999)) expressing yEmRFP from a C. albicans ARS/URA3 plasmid (pCaADH1-yEmRFP, FIG. 7) were grown in YPAD (upper panel) at 30° C. or diluted to 0.4 ODA600 in YPAD+20% bovine calf serum and grown at 37° C. for hyphal induction (lower panel). Cells were washed with PBS and directly viewed by fluorescence microscopy, using an RFP-specific filter set. In contrast to the human codon-optimized mRFP, which is not expressed in C. albicans (data not shown), the yEmRFP could be easily detected in both budding and hyphal cells (FIG. 1A and data not shown). A large percentage of uracil prototrophs of a ura3Δ/ura3Δ C. albicans strain transformed with this ARS URA3 ADH1 promoter-driven yEmRFP plasmid were distinguished by a distinct pale pinkish color (FIG. 1B, upper left panel) and bright fluorescence (FIG. 1B, upper right panel). These colonies did not display the vivid purple color seen by S. cerevisiae, presumably because of lower yEmRFP copy number. When viewed by microscopy, budding C. albicans cells displayed bright cytoplasmic fluorescence that did not diminish even during two hours of hyphal induction; hyphal cells were brightly fluorescent throughout the cell body and filament (FIG. 1A).

TABLE 2

Plasmids

| Name | Features | Reference |
|---|---|---|
| pRS316 | URA3 CEN6 plasmid | Sikorski, R. S. et al., 1989, Genetics 122: 19-27. |
| pRS316-GAP | URA3 CEN6 plasmid containingTDH3pyEmRFP | |
| yEpGAP | URA3 2µ plasmid containing the GAP (TDH3) promoter | Yoko-o, T. et al. 1998, Euro. J. Biochim. 257: 630-7. |
| yEpGAP-Cherry | URA3 2µ plasmid containingTDH3pyEmRFP | |
| yEpGAP-Cherry MCS | URA3 2µ plasmid containingTDH3pyEmRFP and a multiple cloning site | |
| yEpGAP-Cherry GAP-Alg7 | URA3 2µ plasmid containing TDH3p yEmRFP and TDH3p ALG7 | |
| pAW6 | C. albicans ARS URA3 plasmid containing the CaADH1 promoter and GFP | Warenda et al, 2002, Mol. Bio. Cell 13: 2732-46. |
| pCaADH1-Cherry | C. albicans ARS URA3 plasmid containing CaADH1p-yEmRFP | |
| CIp10ΔSac | C. albicans URA3, RP10 integration vector containing a unique SacI restriction site | |
| CIp-ADH1pmCherry | C. albicans URA3, RP10 integration vector containing CaADH1pyEmRFP | |

The 717 base pair yEmRFP open reading frame, flanked by a 5' EcoRI and 3' KpnI site was cloned into yEpGAP (Yoko-o et al. 1998) to construct yEpGAP-Cherry, placing yEmRFP under the transcriptional control of the constitutive TDH3 promoter in a URA3, 2µ plasmid. yEpGAP-Cherry-MCS is exactly like yEpGAP-Cherry, but contains the multiple cloning site from pBluescript SK−, from ClaI to SacI, cloned into the KpnI/SalI site of yEpGAP-Cherry. A NotI/XhoI fragment containing PTDH3-ALG7 was inserted into yEpGAP-Cherry-MCS to create yEpGAP-Cherry GAP-Alg7.

A sectoring assay was performed of C. albicans transformed with an ARS plasmid containing the yEmRFP gene. Yeast containing plasmid-borne yEmRFP gene (yEpGAP-Cherry) were streaked on non-selective medium (YPD) and grown at 30° C. for two days. Purple/white sectored colonies were viewed by light microscopy (FIG. 1B, lower left panel) or fluorescence (FIG. 1B, lower right panel) using a Leica MZFLIII fluorescence stereomicroscope equipped with a JENOPTIK ProgResC14 digital CCD camera. Fluorescence was visualized using a Texas Red filter set and images captured using the ProgRes C14 software (v1.7.1). If the plasmid remained extra chromosomal, then sectored colonies should have arisen when transformed cells were grown in the absence of plasmid selection. The results of this experiment, shown in FIG. 1B, demonstrate that no sectored colonies of C. albicans transformed with yEmRFP on an URA3, ARS containing plasmid could be detected, even after multiple platings on non selective medium. This complete absence of sectoring provides strong genetic evidence that this DNA is stably integrated in chromosome.

Example 2

Purple Color Phenotype in S. Cerevisiae

To rule out the possibility that the yEmRFP induced purple color phenotype in S. cerevisiae was somehow related to the reddish color caused by accumulation of purine precursors in ade2 mutants (Roman, H., Studies of gene mutation in Saccharomyces. Cold Spring Harb Symp Quant Biol 21: 175-185 (1956)), it was demonstrated that a wild type ADE2 (white colored) strain that expresses plasmid-borne yEmRFP is also purple, though of a different hue (FIG. 2A). ADE2 (SEY6210)(Robinson et al., Protein sorting in Saccharomyces cerevisiae: isolation of mutants defective in the delivery and processing of multiple vacuolar hydrolases. Molecular and Cellular Biology 8: 4936-4948 (1988)) or ade2 (W303-1A)(Thomas et al., The genetic control of direct-repeat recombination in Saccharomyces: the effect of rad52 and rad1 on mitotic recombination at GAL10, a transcriptionally regulated gene. Genetics 123: 725-738 (1989)) S. cerevisiae cells were transformed with a URA3-marked 2µ plasmid containing TDH3promoter driven yEmRFP (yEpGAP-Cherry) or the vector (yEpGAP)(Yoko et al., Differences in in vivo acceptor specificity of two galactosyltransferases, the gmh3+ and gma12+ gene products from Schizosaccharomyces pombe. Eur. J. Biochem. 257: 630-637 (1988)), plated on SD(-Ura) plates and incubated for 3 days at 30°. Notably, ade2, ade2 yEmRFP, and ADE2 yEmRFP strains could be easily distinguished from one another by their distinct colony color. A listing of plasmids can be found in FIG. 7.

These differences are exemplified by the spectrum of color phenotypes of the random haploid spores produced from an ADE2/ade2 diploid harboring yEmRFP on a URA3 2µ plasmid (yEpGAP-Cherry) (FIG. 2B). When plated on non-selective medium, the genotype of each colony could be easily assigned based solely on its color phenotype (FIG. 2B). An ADE2/ade2 ura3/ura3 strain containing the 2µ plasmid-borne yEmRFP (yEpGAP-Cherry) was sporulated in 1% potassium acetate. Yeast spores were enriched as described (Rockmill et al., Spore enrichment. Methods Enzymol 194: 146-149 (1991)) and plated on non-selective medium for 5 days to allow ade2-dependent red color to develop. Genotypes of representative colonies are shown. These predicted genotypes were confirmed by plate assays; purple cells were uracil prototrophs and 5-fluoroorotic acid sensitive; red/brown cells were adenine auxotrophs; white cells were uracil auxotrophs and resistant to 5-fluoroorotic acid (data not shown). It was noted that another difference between the purple and red phenotypes in these different strains is color development time; purple cells harboring the yEmRFP plasmid could easily be distinguished from those carrying the vector control plasmid after an overnight incubation, and were vibrant after 2 days, either on plates or in liquid medium. In contrast ade2-dependent red color development required at least three-five days to develop. Taken together, these results demonstrated that the purple color phenotype is due to the expression of yEmRFP. The experiments described below demonstrate the feasibility of using yEmRFP as a phenotypic color marker and further characterize it.

Example 3

Correlation of Purple Color Phenotype and Fluorescent Properties in S. Cerevisiae To determine if the purple color phenotype correlates with the fluorescence properties of mRFP, yeast cells were assayed by fluorescence. Individual cells that expressed yEmRFP on a 2μ plasmid were visualized by fluorescence microscopy. These cells were brightly fluorescent, with a diffuse pattern that appeared largely restricted to the cytoplasm and excluded from the vacuole (FIG. 3A). Cells (SEY6210) harboring the 2μ yEmRFP plasmid (yEpGAP-Cherry) were grown overnight in medium lacking uracil to select for plasmid maintenance. Cells were washed with PBS and directly viewed by fluorescence microscopy, using an RFP-specific filter set. Fluorescence was specific to the emission and excitation spectra of RFP; no bleed-through was observed using GFP or other filter sets.

The correlation between color, fluorescence, and plasmid maintenance was further examined by characterization of the sectoring phenotype of cells harboring the yEmRFP plasmid. If purple color was tightly linked to expression of the yEmRFP gene, then loss of the plasmid carrying this gene would result in white colonies or white sectors that arose from clones within a purple colony that had lost this plasmid. Yeast containing plasmid-borne yEmRFP gene (yEpGAP-Cherry) were streaked on non-selective medium (YPD) and grown at 30° C. for two days. Purple/white sectored colonies were viewed by light microscopy (left panel FIG. 3B) or fluorescence (right panel FIG. 3B) using a Leica MZFLIII fluorescence stereomicroscope equipped with a JENOPTIK ProgResC14 digital CCD camera. Fluorescence was visualized using a Texas Red filter set and images captured using the ProgRes C14 software (v1.7.1). After two days of growth on YPD plates, white and purple/white sectored colonies were detected (FIG. 3B), suggesting that retention of the plasmid carrying yEmRFP is required for purple colony color. Examination of these colonies with an RFP-specific filter also demonstrated that white sectors, as well as white colonies were devoid of fluorescence, while the purple portion of the colonies was brightly fluorescent. These results demonstrate the tight correlation between color, fluorescence and yEmRFP expression.

Figure 7:
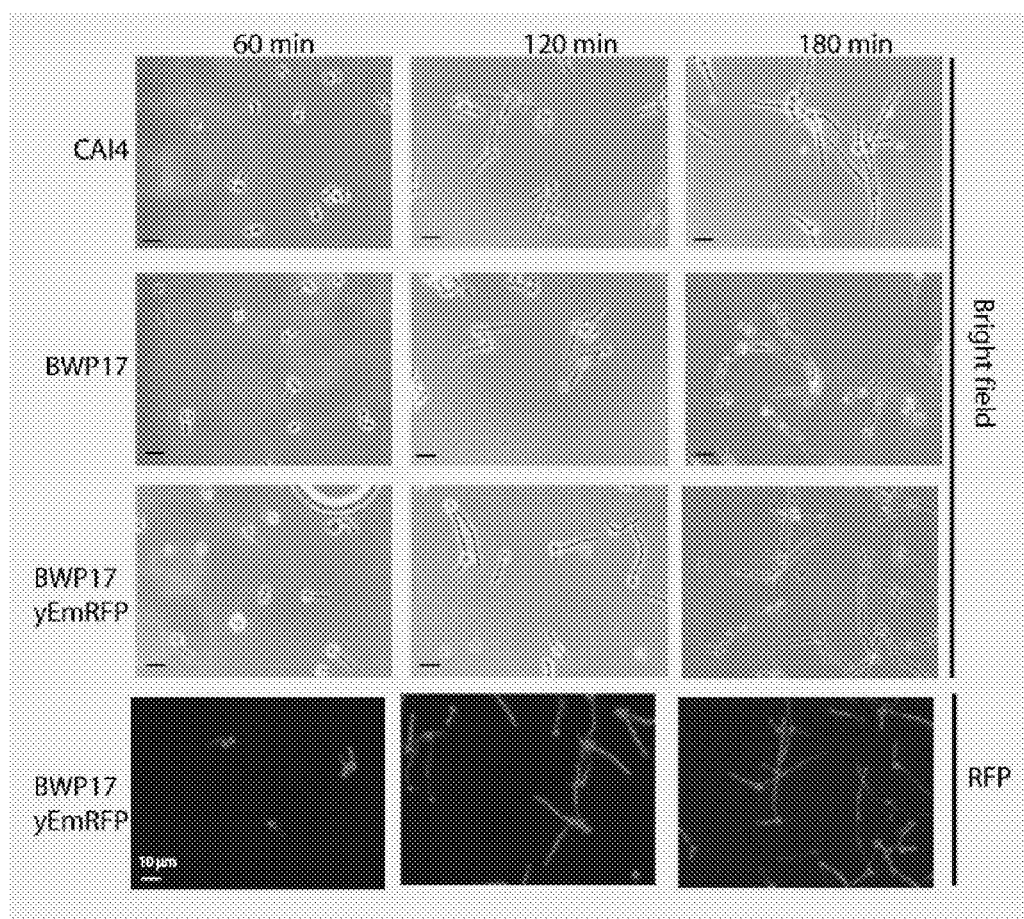
FIG. 7 shows *C. albicans* hyphal induction in control cells (CAI4 and BWP17) and cells expressing yEmRFP.

Fluorescence, colony morphology and sectoring were also examined in yeast expressing yEmRFP from a low copy, CEN vector (pRS316 GAP-Cherry; see FIG. 7). When plated on selective medium, cells expressing yEmRFP at low copy did not display the vivid purple color seen in cells that express yEmRFP from a 2μ plasmid. However, individual cells were still brightly fluorescent when viewed by microscopy (data not shown). Yeast (SEY6210) was transformed with yEmRFP on a URA3/CEN6 vector (pRS316-GAP-mCherry) (FIG. 7). Colonies were plated on non-selective medium and incubated at for two days 30° C. Colonies were analyzed for plasmid loss by a sectoring assay using fluorescence microscopy as described above. When plated on non-selective medium, sectored colonies were also easily detected by fluorescence (FIG. 3C). Taken together, these results demonstrated that the vivid purple colony color requires yEmRFP over expression, but that the more sensitive fluorescence-based assays can be used to monitor plasmid stability of both 2μ and low copy CEN-based plasmids.

Example 4

Visual and Fluorescent Screening of Plasmid Retention in *S. Cerevisiae*

Changes in yEmRFP plasmid-dependent colony color and sectoring phenotypes can be induced by linkage to a gene whose over expression is deleterious. To test if an event that is predicted to bias plasmid retention could be visually screened, yeast were transformed with a plasmid carrying two genes: the yEmRFP gene, and in addition, the PTDH3-driven ALG7 gene whose over expression leads to a mild, dominant negative growth phenotype in wild type cells (C. Noffz, unpublished observations). Cells were transformed with a 2μ yEmRFP plasmid (yEpGAP-Cherry) or the same plasmid containing TDH3 promoter-driven ALG7 (yEpGAP-Cherry GAPALG7). Colony color and fluorescence were monitored visually and by fluorescence as described above. If the purple color phenotype of cells was strictly dependent on plasmid maintenance, then on non selective medium there would be a higher frequency of white colonies and/or colonies with more white sectors that were derived from these cells that would benefit from plasmid loss. The results of this experiment demonstrated that this prediction was borne out. While yeast transformed with plasmids carrying yEmRFP or yEmRFP-PTDH3-ALG7 cells were bright purple on selective medium (not shown), on non selective medium there was a large increase (>500 fold) in the frequency of white colonies from cells transformed with the yEmRFP-PTDH3-ALG7 plasmid compared to those transformed with yEmRFP plasmid (FIG. 3D). In the former case, most cells were white, though some had a slight purplish hue suggesting the residual presence of some yEmRFP-PTDH3-ALG7 plasmids. Indeed, individual sectors of cells retaining this plasmid could be clearly observed by a more sensitive fluorescence assay (FIG. 3D). Taken together, these data demonstrate that cells that maintain this plasmid can be reliably distinguished from those that lose it with high sensitivity, by either a visual or fluorescence assay.

Example 5

No Selective Disadvantages are Conferred by Expression of yEmRFP

Potential selective disadvantage due to expression yEmRFP was investigated. Three aspects of the yeast life cycle were analyzed: cell division, mating, and meiosis. Cell division was assayed by comparing the growth rate during the logarithmic phase of cells harboring the 2μ yEmRFP or parental vector plasmid. In addition, when cells containing the 2μ yEmRFP or parental vector plasmid were co-inoculated in selective medium lacking uracil at a 1:1 ratio, the ratio of purple cells to white cells remained constant over a 36 hour period. The results of these experiments, shown in Table 3, demonstrated no quantitative or qualitative effects of the 2μ yEmRFP plasmid on these processes. Although other biological processes cannot be ruled out, these results suggest that high level expression of yEmRFP does not adversely affect the normal growth and reproductive properties of yeast. Doubling time was calculated by measuring OD600 of yeast grown in SD (-Ura) selective medium at 30° C. during the logarithmic phase of growth period. Deviation is based on two independent experiments. Mating frequency was measured as the percent of prototrophic diploids formed/total viable cells after mating MATα strains (SEY6210) (Robinson et al., Protein sorting in *Saccharomyces cerevisiae*: isolation of mutants defective in the delivery and processing of multiple vacuolar hydrolases. Molecular and Cellular Biology 8: 4936-4948 (1988)) harboring the URA3-marked yEmRFP (yEpGAPCherry) or vector (yEpGAP) to the MATa partner, SEY6211 (Robinson et al. 1988) as described (Sprague., Assay of yeast mating reaction. Methods Enzymol 194: 77-93 (1991)) Shown is the average±standard deviation of duplicate mating determinations. Sporulation efficiency was calculated by determining the percent of sporulated cells in a population of diploids (W303) (n=500) harboring the URA3- marked yEmRFP (yEpGAP-Cherry) or vector (yEpGAP) that had been incubated on sporulation medium (1% potassium acetate) for 5 days at 25° C. Tetrads were monitored visually.

TABLE 3

Effect of yEmRFP expression on growth, mating, and meiosis

| Plasmid | Doubling time [h] | Mating frequency | Sporulation efficiency |
|---|---|---|---|
| yEmRFP | 1.5 ± 0.1 | 21% ± 2% | 18% |
| vector | 1.5 ± 0.1 | 22% ± 2% | 19% |

Example 6

Visual Screening for Transformants in S. Cerevisiae

Figure 4:
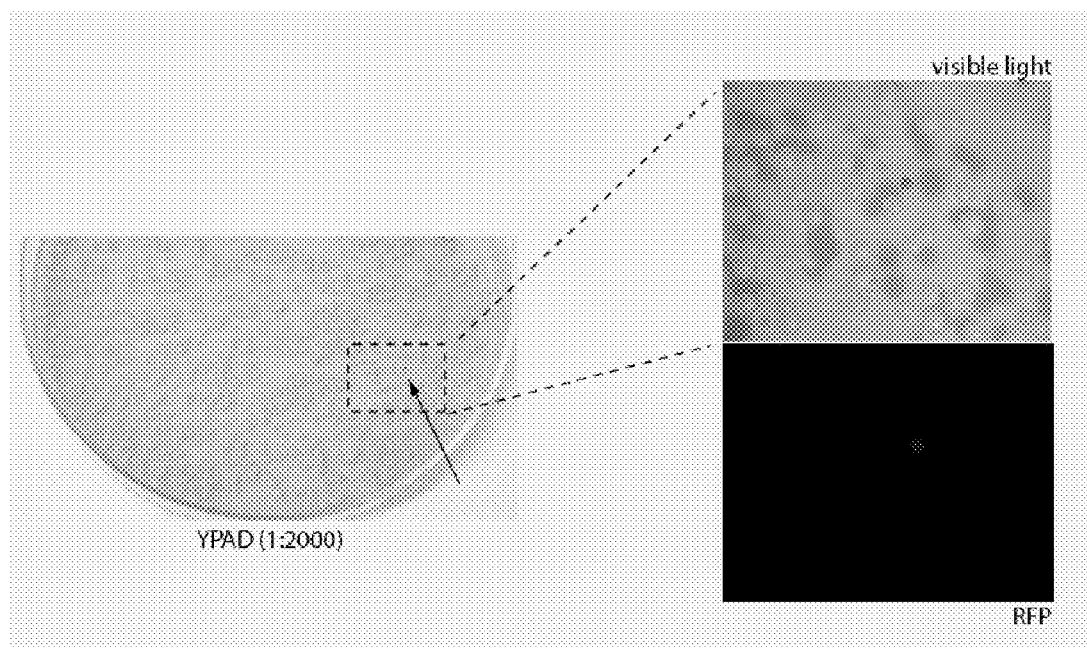
FIG. 4 shows yEmRFP used as a marker to monitor plasmid uptake. *S. cerevisiae* (SEY6210) transformed with a URA3-marked 2μ plasmid carrying yEmRFP (yEpGAPcherry) were diluted 1:2000 with untransformed cells and plated at a frequency predicted to yield one or less yEmRFP-expressing cell per plate.

Because of the rapidity of color development and the ease of detection, the yEmRFP expression can be used as a visual screen to identify yeast transformants, much like the blue-white color associated with lacZ-encoded β-galactosidase production in bacteria (although without the need for chromogenic additives). S. cerevisiae (SEY6210) transformed with a URA3-marked 2μ plasmid carrying yEmRFP (yEpGAPcherry) were diluted 1:2000 with untransformed cells and plated on YPAD at a frequency predicted to yield one or less yEmRFP-expressing cell per plate. Plates were incubated for 2 days at 30°. Fluorescence was visualized as described above. Based on this dilution and the number of cells plated, it was calculated that there would be one or less purple colony per plate. As shown in FIG. 4, a single purple colony per plate could be easily identified, both visually and by fluorescence under these conditions. Further dilutions, taken out to 1:10,000 demonstrated that the sensitivity of this plate assay is limited by colony size, and hence the number of colonies that can be plated. In the case of S. cerevisiae, confluence of individual colonies occurs beyond about 5000 colonies/100 mm plate (FIG. 4). Nevertheless, these results demonstrate that individual colonies can be detected with high specificity.

Example 7

Expression in Candida Albicans of Multiple mRFP Variants

The isolated nucleic acid sequences of mRFP variants, such as mStrawberry, mTangerine, mOrange, mBanana and mHoneydew, are recoded by methods known to one of ordinary skill in the art so that the sequences are adapted to expression by the non-canonical C. albicans DNA expression system, as has been described herein with regard to mCherry. The C. albicans-adapted nucleic acids sequences of the mRFP variants are linked to an operable promoter in a vector by means known to one of ordinary skill in the art. A vector containing the C. albicans-adapted nucleic acid sequence of an mRFP variant is transformed into C. albicans cells, which are grown in suitable media in accordance with methods known to one of ordinary skill in the art. The expression of an mRFP variant in C. albicans can be detected by fluorescent assays at suitable wavelengths, as known to one of ordinary skill in the art. In combination with other mRFP variants expressed in C. albicans, the mRFP variants may be used to perform two or more color fluorescent assays by means known to one of ordinary skill in the art.

Example 8

Expression of yEmRFP has No Affect on the Rate or Length of Hyphal Formation

Candida is dimorphic and exhibits a spherical form and a hyphal form. Infection often occurs by extension of hyphae into skin or tissue. Individual yeast cells grown at 30° C. were seeded on glass cover slips as described (Rida et al., 2006, Mol. Biol. Cell 17, 4364-78). Hyphal growth was induced by the addition of medium containing 10% bovine calf serum and shifting the growth temperature to 37° C. At various times after hyphal induction (FIG. 7), cover slips were removed, mounted on glass slides and viewed by light or fluorescence microscopy. As shown, expression of a yEmRFP did not affect hyphal formation.

Example 9

Visualization of Fungal Infection in Host Tissue

Overnight cultures of BWP17, CAI4, or isogenic prototrophic variants expressing yEmRFP(SKY38, SKY39, SKY40) were washed twice with sterile water and resuspended at $10^7$ cells per ml in sterile water. Mice (BALB/C) were injected with 100 μl of yeast ($10^6$ cells) in the lateral tail vein. Infected mice were monitored twice daily. In vivo fluorescence analysis of sedated whole animals was performed on a multispectral Meastro System, using excitation RFP-optimized wavelengths. When considered moribund (typically between days 2-4 post infection), mice were euthanized by anesthetization followed by cervical dislocation. All experimental procedures were carried out according to the NIH guidelines for the ethical treatment of animals.

The kidneys from control infected mice were analyzed in two ways. One kidney was homogenized in PBS, diluted, and plated on YPD to determine genotype, phenotype, and fungal load (expressed as CFU/gram of kidney tissue). The other kidney was used for imaging by fluorescence microscopy (FIG. 8), using a low magnification (4× objective) Zeiss fluorescent dissecting microscope. After imaging the surface of the kidney with light or RFP-specific filters, the kidney was sliced longitudinally in half to image its interior. Fluorescent foci were picked out manually and individual cells analyzed by higher magnification (40× or 100×) fluorescence microscopy.

Example 10

Macrophage Uptake of Yeast Cells

Phagocytosis of fluorescent C. albicans by the mouse BALB/C macrophage cell line J774 was performed as follows. J774 cells were maintained in DMEM+10% horse serum+ and incubated at 37° C. in the presence of 5% CO2. Pre-confluent cultures (grown to about $5 \times 10^5$ cells/plate) were diluted and plated on cover slips in 24-well plates (~$10^4$ cells/well). After 24 hours incubation, fresh overnight cultures of yeast (SKY40 that had been washed twice in PBS and resuspended at 1OD$_{600}$/ml in PBS) were added to each well at various multiplicities of infection. After allowing yeast to adhere to macrophages for 5-10 minutes, wells were washed and fresh $CO_2$-independent DMEM+10% horse serum was added and plates were incubated at 37° C. At various times post-infection, Calcofluor white (SIGMA) 1 μg/ml final concentration) or PSA-FITC(SIGMA, 1:1000 dilution) was added. After 1-5 minutes, cover slips were mounted on a glass slide, and viewed by fluorescence microscopy. The addition of these reagents allow us to distinguish yeast cells that are internalized by macrophages from those that are simply adhering to the cell surface. (FIG. 9).

What is claimed is:

1. An isolated nucleic acid comprising the nucleic acid sequence of SEQ ID NO:1, SEQ ID NO:3, SEQ ID NO:5, SEQ ID NO:7, or SEQ ID NO:9, or the full length complement thereof.

2. The isolated nucleic acid molecule of claim 1, which further comprises an expression control sequence.

3. A host cell comprising the nucleic acid of claim 1.

4. The host cell of claim 3, wherein the host cell is *E. coli*.

5. The host cell of claim 3, wherein the host cell is *S. cerevisiae*.

6. The host cell of claim 3, wherein the host cell is *C. albicans*.

7. A vector comprising the nucleic acid of claim 1.

8. A host cell comprising the vector of claim 7.

9. The host cell of claim 8, wherein the host cell is *E. coli*.

10. The host cell of claim 8, wherein the host cell is *S. cerevisiae*.

11. A kit comprising the vector of claim 7.

12. A kit comprising the host cell of claim 3.

13. The kit of claim 12, wherein the host cell is *C. albicans*.

14. The kit of claim 12, wherein the host cell is *S. cerevisae*.

15. The host cell of claim 8, wherein the host cell is *C. albicans*.

* * * * *

```
                          SEQUENCE LISTING

<160> NUMBER OF SEQ ID NOS: 12

<210> SEQ ID NO 1
<211> LENGTH: 711
<212> TYPE: DNA
<213> ORGANISM: unknown
<220> FEATURE:
<223> OTHER INFORMATION: synthetic
<220> FEATURE:
<221> NAME/KEY: CDS
<222> LOCATION: (1)..(711)

<400> SEQUENCE: 1 atg gtt tca aaa ggt gaa gaa gat aat atg gct att att aaa gaa ttt      48
Met Val Ser Lys Gly Glu Glu Asp Asn Met Ala Ile Ile Lys Glu Phe
1               5                   10                  15 atg aga ttt aaa gtt cat atg gaa ggt tca gtt aat ggt cat gaa ttt      96
Met Arg Phe Lys Val His Met Glu Gly Ser Val Asn Gly His Glu Phe
                20                  25                  30 gaa att gaa ggt gaa ggt gaa ggt aga cca tat gaa ggt act caa act     144
Glu Ile Glu Gly Glu Gly Glu Gly Arg Pro Tyr Glu Gly Thr Gln Thr
            35                  40                  45 gct aaa ttg aaa gtt act aaa ggt ggt cca tta cca ttt gct tgg gat     192
Ala Lys Leu Lys Val Thr Lys Gly Gly Pro Leu Pro Phe Ala Trp Asp
        50                  55                  60 att ttg tca cca caa ttt atg tat ggt tca aaa gct tat gtt aaa cat     240
Ile Leu Ser Pro Gln Phe Met Tyr Gly Ser Lys Ala Tyr Val Lys His
65                  70                  75                  80 cca gct gat att cca gat tat tta aaa ttg tca ttt cca gaa ggt ttt     288
Pro Ala Asp Ile Pro Asp Tyr Leu Lys Leu Ser Phe Pro Glu Gly Phe
                85                  90                  95 aaa tgg gaa aga gtt atg aat ttt gaa gat ggt ggt gtt gtt act gtt     336
Lys Trp Glu Arg Val Met Asn Phe Glu Asp Gly Gly Val Val Thr Val
            100                 105                 110 act caa gat tca tca tta caa gat ggt gaa ttt att tat aaa gtt aaa     384
Thr Gln Asp Ser Ser Leu Gln Asp Gly Glu Phe Ile Tyr Lys Val Lys
        115                 120                 125 ttg aga ggt act aat ttt cca tca gat ggt cca gtt atg caa aaa aaa     432
Leu Arg Gly Thr Asn Phe Pro Ser Asp Gly Pro Val Met Gln Lys Lys
    130                 135                 140 act atg ggt tgg gaa gct tca tca gaa aga atg tat cca gaa gat ggt     480
Thr Met Gly Trp Glu Ala Ser Ser Glu Arg Met Tyr Pro Glu Asp Gly
145                 150                 155                 160 gct tta aaa ggt gaa att aaa caa aga ttg aaa tta aaa gat ggt ggt     528
Ala Leu Lys Gly Glu Ile Lys Gln Arg Leu Lys Leu Lys Asp Gly Gly
                165                 170                 175 cat tat gat gct gaa gtt aaa act act tat aaa gct aaa aaa cca gtt     576
His Tyr Asp Ala Glu Val Lys Thr Thr Tyr Lys Ala Lys Lys Pro Val
            180                 185                 190 caa tta cca ggt gct tat aat gtt aat att aaa ttg gat att act tca     624
Gln Leu Pro Gly Ala Tyr Asn Val Asn Ile Lys Leu Asp Ile Thr Ser
        195                 200                 205 cat aat gaa gat tat act att gtt gaa caa tat gaa aga gct gaa ggt     672
His Asn Glu Asp Tyr Thr Ile Val Glu Gln Tyr Glu Arg Ala Glu Gly
    210                 215                 220 aga cat tca act ggt ggt atg gat gaa tta tat aaa taa               711
Arg His Ser Thr Gly Gly Met Asp Glu Leu Tyr Lys
225                 230                 235
```

```
<210> SEQ ID NO 2
<211> LENGTH: 236
<212> TYPE: PRT
<213> ORGANISM: unknown
<220> FEATURE:
<223> OTHER INFORMATION: Synthetic Construct

<400> SEQUENCE: 2

Met Val Ser Lys Gly Glu Glu Asp Asn Met Ala Ile Ile Lys Glu Phe
1               5                   10                  15

Met Arg Phe Lys Val His Met Glu Gly Ser Val Asn Gly His Glu Phe
                20                  25                  30

Glu Ile Glu Gly Glu Gly Glu Gly Arg Pro Tyr Glu Gly Thr Gln Thr
            35                  40                  45

Ala Lys Leu Lys Val Thr Lys Gly Gly Pro Leu Pro Phe Ala Trp Asp
    50                  55                  60

Ile Leu Ser Pro Gln Phe Met Tyr Gly Ser Lys Ala Tyr Val Lys His
65                  70                  75                  80

Pro Ala Asp Ile Pro Asp Tyr Leu Lys Leu Ser Phe Pro Glu Gly Phe
                85                  90                  95

Lys Trp Glu Arg Val Met Asn Phe Glu Asp Gly Gly Val Val Thr Val
                100                 105                 110

Thr Gln Asp Ser Ser Leu Gln Asp Gly Glu Phe Ile Tyr Lys Val Lys
            115                 120                 125

Leu Arg Gly Thr Asn Phe Pro Ser Asp Gly Pro Val Met Gln Lys Lys
    130                 135                 140

Thr Met Gly Trp Glu Ala Ser Ser Glu Arg Met Tyr Pro Glu Asp Gly
145                 150                 155                 160

Ala Leu Lys Gly Glu Ile Lys Gln Arg Leu Lys Leu Lys Asp Gly Gly
                165                 170                 175

His Tyr Asp Ala Glu Val Lys Thr Thr Tyr Lys Ala Lys Lys Pro Val
            180                 185                 190

Gln Leu Pro Gly Ala Tyr Asn Val Asn Ile Lys Leu Asp Ile Thr Ser
    195                 200                 205

His Asn Glu Asp Tyr Thr Ile Val Glu Gln Tyr Glu Arg Ala Glu Gly
210                 215                 220

Arg His Ser Thr Gly Gly Met Asp Glu Leu Tyr Lys
225                 230                 235

<210> SEQ ID NO 3
<211> LENGTH: 711
<212> TYPE: DNA
<213> ORGANISM: unknown
<220> FEATURE:
<223> OTHER INFORMATION: synthetic
<220> FEATURE:
<221> NAME/KEY: CDS
<222> LOCATION: (1)..(711)

<400> SEQUENCE: 3 atg gtt tca aaa ggt gaa gaa aat aat atg gct att att aaa gaa ttt     48
Met Val Ser Lys Gly Glu Glu Asn Asn Met Ala Ile Ile Lys Glu Phe
1               5                   10                  15 atg aga ttt aaa gtt aga atg gaa ggt tca gtt aat ggt cat gaa ttt     96
Met Arg Phe Lys Val Arg Met Glu Gly Ser Val Asn Gly His Glu Phe
                20                  25                  30 gaa att gaa ggt gaa ggt gaa ggt aga cca tat gaa ggt act caa act    144
Glu Ile Glu Gly Glu Gly Glu Gly Arg Pro Tyr Glu Gly Thr Gln Thr
            35                  40                  45
```

```
gct aaa ttg aaa gtt act aaa ggt ggt cca tta cca ttt gct tgg gat    192
Ala Lys Leu Lys Val Thr Lys Gly Gly Pro Leu Pro Phe Ala Trp Asp
 50                  55                  60 att ttg act cca aat ttt act tat ggt tca aaa gct tat gtt aaa cat    240
Ile Leu Thr Pro Asn Phe Thr Tyr Gly Ser Lys Ala Tyr Val Lys His
 65                  70                  75                  80 cca gct gat att cca gat tat tta aaa ttg tca ttt cca gaa ggt ttt    288
Pro Ala Asp Ile Pro Asp Tyr Leu Lys Leu Ser Phe Pro Glu Gly Phe
                 85                  90                  95 aaa tgg gaa aga gtt atg aat ttt gaa gat ggt ggt gtt gtt act gtt    336
Lys Trp Glu Arg Val Met Asn Phe Glu Asp Gly Gly Val Val Thr Val
            100                 105                 110 act caa gat tca tca tta caa gat ggt gaa ttt att tat aaa gtt aaa    384
Thr Gln Asp Ser Ser Leu Gln Asp Gly Glu Phe Ile Tyr Lys Val Lys
        115                 120                 125 ttg aga ggt act aat ttt cca tca gat ggt cca gtt atg caa aaa aaa    432
Leu Arg Gly Thr Asn Phe Pro Ser Asp Gly Pro Val Met Gln Lys Lys
    130                 135                 140 act atg ggt tgg gaa gct tca tca gaa aga atg tat cca gaa gat ggt    480
Thr Met Gly Trp Glu Ala Ser Ser Glu Arg Met Tyr Pro Glu Asp Gly
145                 150                 155                 160 gct tta aaa ggt gaa att aaa atg aga ttg aaa tta aaa gat ggt ggt    528
Ala Leu Lys Gly Glu Ile Lys Met Arg Leu Lys Leu Lys Asp Gly Gly
                165                 170                 175 cat tat gat gct gaa gtt aaa act act tat aaa gct aaa aaa cca gtt    576
His Tyr Asp Ala Glu Val Lys Thr Thr Tyr Lys Ala Lys Lys Pro Val
            180                 185                 190 caa tta cca ggt gct tat att gtt ggt att aaa ttg gat att act tca    624
Gln Leu Pro Gly Ala Tyr Ile Val Gly Ile Lys Leu Asp Ile Thr Ser
        195                 200                 205 cat aat gaa gat tat act att gtt gaa ttg tat gaa aga gct gaa ggt    672
His Asn Glu Asp Tyr Thr Ile Val Glu Leu Tyr Glu Arg Ala Glu Gly
    210                 215                 220 aga cat tca act ggt ggt atg gat gaa tta tat aaa taa                711
Arg His Ser Thr Gly Gly Met Asp Glu Leu Tyr Lys
225                 230                 235
```

<210> SEQ ID NO 4
<211> LENGTH: 236
<212> TYPE: PRT
<213> ORGANISM: unknown
<220> FEATURE:
<223> OTHER INFORMATION: Synthetic Construct

<400> SEQUENCE: 4

```
Met Val Ser Lys Gly Glu Glu Asn Asn Met Ala Ile Ile Lys Glu Phe
 1               5                  10                  15

Met Arg Phe Lys Val Arg Met Glu Gly Ser Val Asn Gly His Glu Phe
                20                  25                  30

Glu Ile Glu Gly Glu Gly Glu Gly Arg Pro Tyr Glu Gly Thr Gln Thr
            35                  40                  45

Ala Lys Leu Lys Val Thr Lys Gly Gly Pro Leu Pro Phe Ala Trp Asp
 50                  55                  60

Ile Leu Thr Pro Asn Phe Thr Tyr Gly Ser Lys Ala Tyr Val Lys His
 65                  70                  75                  80

Pro Ala Asp Ile Pro Asp Tyr Leu Lys Leu Ser Phe Pro Glu Gly Phe
                 85                  90                  95

Lys Trp Glu Arg Val Met Asn Phe Glu Asp Gly Gly Val Val Thr Val
            100                 105                 110
```

```
Thr Gln Asp Ser Ser Leu Gln Asp Gly Glu Phe Ile Tyr Lys Val Lys
            115                 120                 125

Leu Arg Gly Thr Asn Phe Pro Ser Asp Gly Pro Val Met Gln Lys Lys
        130                 135                 140

Thr Met Gly Trp Glu Ala Ser Ser Glu Arg Met Tyr Pro Glu Asp Gly
145                 150                 155                 160

Ala Leu Lys Gly Glu Ile Lys Met Arg Leu Lys Leu Lys Asp Gly Gly
                165                 170                 175

His Tyr Asp Ala Glu Val Lys Thr Thr Tyr Lys Ala Lys Lys Pro Val
            180                 185                 190

Gln Leu Pro Gly Ala Tyr Ile Val Gly Ile Lys Leu Asp Ile Thr Ser
        195                 200                 205

His Asn Glu Asp Tyr Thr Ile Val Glu Leu Tyr Glu Arg Ala Glu Gly
    210                 215                 220

Arg His Ser Thr Gly Gly Met Asp Glu Leu Tyr Lys
225                 230                 235

<210> SEQ ID NO 5
<211> LENGTH: 711
<212> TYPE: DNA
<213> ORGANISM: unknown
<220> FEATURE:
<223> OTHER INFORMATION: synthetic
<220> FEATURE:
<221> NAME/KEY: CDS
<222> LOCATION: (1)..(711)

<400> SEQUENCE: 5 atg gtt tca aaa ggt gaa gaa aat aat atg gct att att aaa gaa ttt       48
Met Val Ser Lys Gly Glu Glu Asn Asn Met Ala Ile Ile Lys Glu Phe
1               5                   10                  15 atg aga ttt aaa gtt aga atg gaa ggt tca gtt aat ggt cat gaa ttt       96
Met Arg Phe Lys Val Arg Met Glu Gly Ser Val Asn Gly His Glu Phe
                20                  25                  30 gaa att gaa ggt gaa ggt gaa ggt aga cca tat gaa ggt ttt caa act      144
Glu Ile Glu Gly Glu Gly Glu Gly Arg Pro Tyr Glu Gly Phe Gln Thr
            35                  40                  45 gct aaa ttg aaa gtt act aaa ggt gga cca tta cca ttt gct tgg gat      192
Ala Lys Leu Lys Val Thr Lys Gly Gly Pro Leu Pro Phe Ala Trp Asp
        50                  55                  60 att ttg tca cca caa ttt act tat ggt tca aaa gct tat gtt aaa cat      240
Ile Leu Ser Pro Gln Phe Thr Tyr Gly Ser Lys Ala Tyr Val Lys His
65                  70                  75                  80 cca gct gat att cca gat tat ttt aaa ttg tca ttt cca gaa ggt ttt      288
Pro Ala Asp Ile Pro Asp Tyr Phe Lys Leu Ser Phe Pro Glu Gly Phe
                85                  90                  95 aaa tgg gaa aga gtt atg aat ttt gaa gat ggt ggt gtt gtt act gtt      336
Lys Trp Glu Arg Val Met Asn Phe Glu Asp Gly Gly Val Val Thr Val
            100                 105                 110 act caa gat tca tca tta caa gat ggt gaa ttt att tat aaa gtt aaa      384
Thr Gln Asp Ser Ser Leu Gln Asp Gly Glu Phe Ile Tyr Lys Val Lys
        115                 120                 125 ttg aga ggt act aat ttt cca tca gat ggt cca gtt atg caa aaa aaa      432
Leu Arg Gly Thr Asn Phe Pro Ser Asp Gly Pro Val Met Gln Lys Lys
    130                 135                 140 act atg ggt tgg gaa gct tca tca gaa aga atg tat cca gaa gat ggt      480
Thr Met Gly Trp Glu Ala Ser Ser Glu Arg Met Tyr Pro Glu Asp Gly
145                 150                 155                 160 gct tta aaa ggt gaa att aaa atg aga ttg aaa tta aaa gat ggt ggt      528
Ala Leu Lys Gly Glu Ile Lys Met Arg Leu Lys Leu Lys Asp Gly Gly
```

```
                                    165                    170                   175
cat tat act tca gaa gtt aaa act act tat aaa gct aaa aaa cca gtt          576
His Tyr Thr Ser Glu Val Lys Thr Thr Tyr Lys Ala Lys Lys Pro Val
            180                     185                    190 caa tta cca ggt gct tat att gtt ggt att aaa ttg gat att act tca          624
Gln Leu Pro Gly Ala Tyr Ile Val Gly Ile Lys Leu Asp Ile Thr Ser
        195                     200                     205 cat aat gaa gat tat act att gtt gaa caa tat gaa aga gct gaa ggt          672
His Asn Glu Asp Tyr Thr Ile Val Glu Gln Tyr Glu Arg Ala Glu Gly
    210                     215                     220 aga cat tca act ggt ggt atg gat gaa tta tat aaa taa                      711
Arg His Ser Thr Gly Gly Met Asp Glu Leu Tyr Lys
225                 230                 235

<210> SEQ ID NO 6
<211> LENGTH: 236
<212> TYPE: PRT
<213> ORGANISM: unknown
<220> FEATURE:
<223> OTHER INFORMATION: Synthetic Construct

<400> SEQUENCE: 6

Met Val Ser Lys Gly Glu Glu Asn Asn Met Ala Ile Ile Lys Glu Phe
1               5                   10                  15

Met Arg Phe Lys Val Arg Met Glu Gly Ser Val Asn Gly His Glu Phe
            20                  25                  30

Glu Ile Glu Gly Glu Gly Glu Gly Arg Pro Tyr Glu Gly Phe Gln Thr
        35                  40                  45

Ala Lys Leu Lys Val Thr Lys Gly Gly Pro Leu Pro Phe Ala Trp Asp
    50                  55                  60

Ile Leu Ser Pro Gln Phe Thr Tyr Gly Ser Lys Ala Tyr Val Lys His
65                  70                  75                  80

Pro Ala Asp Ile Pro Asp Tyr Phe Lys Leu Ser Phe Pro Glu Gly Phe
                85                  90                  95

Lys Trp Glu Arg Val Met Asn Phe Glu Asp Gly Gly Val Val Thr Val
            100                 105                 110

Thr Gln Asp Ser Ser Leu Gln Asp Gly Glu Phe Ile Tyr Lys Val Lys
        115                 120                 125

Leu Arg Gly Thr Asn Phe Pro Ser Asp Gly Pro Val Met Gln Lys Lys
    130                 135                 140

Thr Met Gly Trp Glu Ala Ser Ser Glu Arg Met Tyr Pro Glu Asp Gly
145                 150                 155                 160

Ala Leu Lys Gly Glu Ile Lys Met Arg Leu Lys Leu Lys Asp Gly Gly
                165                 170                 175

His Tyr Thr Ser Glu Val Lys Thr Thr Tyr Lys Ala Lys Lys Pro Val
            180                 185                 190

Gln Leu Pro Gly Ala Tyr Ile Val Gly Ile Lys Leu Asp Ile Thr Ser
        195                 200                 205

His Asn Glu Asp Tyr Thr Ile Val Glu Gln Tyr Glu Arg Ala Glu Gly
    210                 215                 220

Arg His Ser Thr Gly Gly Met Asp Glu Leu Tyr Lys
225                 230                 235

<210> SEQ ID NO 7
<211> LENGTH: 711
<212> TYPE: DNA
<213> ORGANISM: unknown
<220> FEATURE:
```

<223> OTHER INFORMATION: synthetic
<220> FEATURE:
<221> NAME/KEY: CDS
<222> LOCATION: (1)..(711)

<400> SEQUENCE: 7

```
atg gtt tca aaa ggt gaa gaa aat aat atg gct gtt att aaa gaa ttt      48
Met Val Ser Lys Gly Glu Glu Asn Asn Met Ala Val Ile Lys Glu Phe
1               5                   10                  15 atg aga ttt aaa gtt aga atg gaa ggt tca gtt aat ggt cat gaa ttt      96
Met Arg Phe Lys Val Arg Met Glu Gly Ser Val Asn Gly His Glu Phe
                20                  25                  30 gaa att gaa ggt gaa ggt gaa ggt aga cca tat gaa ggt act caa act     144
Glu Ile Glu Gly Glu Gly Glu Gly Arg Pro Tyr Glu Gly Thr Gln Thr
            35                  40                  45 gct aaa ttg aaa gtt act aaa ggt gga cca tta cca ttt gct tgg gat     192
Ala Lys Leu Lys Val Thr Lys Gly Gly Pro Leu Pro Phe Ala Trp Asp
        50                  55                  60 att ttg tca cca caa ttt tgt tat ggt tca aaa gct tat gtt aaa cat     240
Ile Leu Ser Pro Gln Phe Cys Tyr Gly Ser Lys Ala Tyr Val Lys His
65                  70                  75                  80 cca act ggt att cca gat tat ttt aaa ttg tca ttt cca gaa ggt ttt     288
Pro Thr Gly Ile Pro Asp Tyr Phe Lys Leu Ser Phe Pro Glu Gly Phe
                85                  90                  95 aaa tgg gaa aga gtt atg aat ttt gaa gat ggt ggt gtt gtt act gtt     336
Lys Trp Glu Arg Val Met Asn Phe Glu Asp Gly Gly Val Val Thr Val
                100                 105                 110 gct caa gat tca tca tta caa gat ggt gaa ttt att tat aaa gtt aaa     384
Ala Gln Asp Ser Ser Leu Gln Asp Gly Glu Phe Ile Tyr Lys Val Lys
            115                 120                 125 ttg aga ggt act aat ttt cca tca gat ggt cca gtt atg caa aaa aaa     432
Leu Arg Gly Thr Asn Phe Pro Ser Asp Gly Pro Val Met Gln Lys Lys
        130                 135                 140 act atg ggt tgg gaa gct tca tca gaa aga atg tat cca gaa gat ggt     480
Thr Met Gly Trp Glu Ala Ser Ser Glu Arg Met Tyr Pro Glu Asp Gly
145                 150                 155                 160 gct tta aaa ggt gaa att aaa atg aga ttg aaa tta aaa gat ggt ggt     528
Ala Leu Lys Gly Glu Ile Lys Met Arg Leu Lys Leu Lys Asp Gly Gly
                165                 170                 175 cat tat tca gct gaa act aaa act act tat aaa gct aaa aaa cca gtt     576
His Tyr Ser Ala Glu Thr Lys Thr Thr Tyr Lys Ala Lys Lys Pro Val
                180                 185                 190 caa tta cca ggt gct tat att gct ggt gaa aaa att gat att act tca     624
Gln Leu Pro Gly Ala Tyr Ile Ala Gly Glu Lys Ile Asp Ile Thr Ser
            195                 200                 205 cat aat gaa gat tat act att gtt gaa ttg tat gaa aga gct gaa ggt     672
His Asn Glu Asp Tyr Thr Ile Val Glu Leu Tyr Glu Arg Ala Glu Gly
        210                 215                 220 aga cat tca act ggt ggt atg gat gaa tta tat aaa taa                 711
Arg His Ser Thr Gly Gly Met Asp Glu Leu Tyr Lys
225                 230                 235
```

<210> SEQ ID NO 8
<211> LENGTH: 236
<212> TYPE: PRT
<213> ORGANISM: unknown
<220> FEATURE:
<223> OTHER INFORMATION: Synthetic Construct

<400> SEQUENCE: 8

```
Met Val Ser Lys Gly Glu Glu Asn Asn Met Ala Val Ile Lys Glu Phe
1               5                   10                  15
```

```
Met Arg Phe Lys Val Arg Met Glu Gly Ser Val Asn Gly His Glu Phe
         20                  25                  30

Glu Ile Glu Gly Glu Gly Glu Gly Arg Pro Tyr Glu Gly Thr Gln Thr
             35                  40                  45

Ala Lys Leu Lys Val Thr Lys Gly Gly Pro Leu Pro Phe Ala Trp Asp
 50                  55                  60

Ile Leu Ser Pro Gln Phe Cys Tyr Gly Ser Lys Ala Tyr Val Lys His
 65                  70                  75                  80

Pro Thr Gly Ile Pro Asp Tyr Phe Lys Leu Ser Phe Pro Glu Gly Phe
                 85                  90                  95

Lys Trp Glu Arg Val Met Asn Phe Glu Asp Gly Gly Val Val Thr Val
                100                 105                 110

Ala Gln Asp Ser Ser Leu Gln Asp Gly Glu Phe Ile Tyr Lys Val Lys
            115                 120                 125

Leu Arg Gly Thr Asn Phe Pro Ser Asp Gly Pro Val Met Gln Lys Lys
130                 135                 140

Thr Met Gly Trp Glu Ala Ser Ser Glu Arg Met Tyr Pro Glu Asp Gly
145                 150                 155                 160

Ala Leu Lys Gly Glu Ile Lys Met Arg Leu Lys Leu Lys Asp Gly Gly
                165                 170                 175

His Tyr Ser Ala Glu Thr Lys Thr Thr Tyr Lys Ala Lys Lys Pro Val
            180                 185                 190

Gln Leu Pro Gly Ala Tyr Ile Ala Gly Glu Lys Ile Asp Ile Thr Ser
        195                 200                 205

His Asn Glu Asp Tyr Thr Ile Val Glu Leu Tyr Glu Arg Ala Glu Gly
    210                 215                 220

Arg His Ser Thr Gly Gly Met Asp Glu Leu Tyr Lys
225                 230                 235

<210> SEQ ID NO 9
<211> LENGTH: 711
<212> TYPE: DNA
<213> ORGANISM: unknown
<220> FEATURE:
<223> OTHER INFORMATION: synthetic
<220> FEATURE:
<221> NAME/KEY: CDS
<222> LOCATION: (1)..(711)

<400> SEQUENCE: 9 atg gtt tca aaa ggt gaa gaa aat aat atg gct att att aaa gaa ttt      48
Met Val Ser Lys Gly Glu Glu Asn Asn Met Ala Ile Ile Lys Glu Phe
1               5                  10                  15 atg aga ttt aaa gtt cat gtt gaa ggt tca gtt aat ggt cat gaa ttt      96
Met Arg Phe Lys Val His Val Glu Gly Ser Val Asn Gly His Glu Phe
             20                  25                  30 gaa att gaa ggt gaa ggt gaa ggt aga cca tat gaa ggt act caa act     144
Glu Ile Glu Gly Glu Gly Glu Gly Arg Pro Tyr Glu Gly Thr Gln Thr
         35                  40                  45 gct aaa ttg aaa gtt act aaa ggt gga cca tta cca ttt act tgg gat     192
Ala Lys Leu Lys Val Thr Lys Gly Gly Pro Leu Pro Phe Thr Trp Asp
 50                  55                  60 att ttg tca cca caa ttt atg ttt ggt tca aaa gtt tat att aaa cat     240
Ile Leu Ser Pro Gln Phe Met Phe Gly Ser Lys Val Tyr Ile Lys His
 65                  70                  75                  80 cca gct gat att cca gat tat ttt aaa ttg tca ttt cca gaa ggt ttt     288
Pro Ala Asp Ile Pro Asp Tyr Phe Lys Leu Ser Phe Pro Glu Gly Phe
                 85                  90                  95
```

```
aga tgg gaa aga gtt atg aat ttt gaa gat ggt ggt gtt gtt act gtt      336
Arg Trp Glu Arg Val Met Asn Phe Glu Asp Gly Gly Val Val Thr Val
            100                 105                 110 act caa gat tca tca tta caa gat ggt gtt ttt att tat aaa gtt aaa      384
Thr Gln Asp Ser Ser Leu Gln Asp Gly Val Phe Ile Tyr Lys Val Lys
        115                 120                 125 ttg aga ggt act aat ttt cca tca gat ggt cca gtt atg caa tgt aga      432
Leu Arg Gly Thr Asn Phe Pro Ser Asp Gly Pro Val Met Gln Cys Arg
    130                 135                 140 act atg ggt tgg gaa gct ttt act gaa aga atg tat cca gaa gat ggt      480
Thr Met Gly Trp Glu Ala Phe Thr Glu Arg Met Tyr Pro Glu Asp Gly
145                 150                 155                 160 gct tta aaa tca gaa att aaa act aga ttg aaa tta aaa gat ggt ggt      528
Ala Leu Lys Ser Glu Ile Lys Thr Arg Leu Lys Leu Lys Asp Gly Gly
                165                 170                 175 cat tat gat gct gaa gtt aaa act act tat aaa gct aaa aaa cca gtt      576
His Tyr Asp Ala Glu Val Lys Thr Thr Tyr Lys Ala Lys Lys Pro Val
            180                 185                 190 caa tta cca ggt gct tat aat gtt gat att aaa ttg gat att gtt tca      624
Gln Leu Pro Gly Ala Tyr Asn Val Asp Ile Lys Leu Asp Ile Val Ser
        195                 200                 205 cat aat gaa gat tat act att gtt gaa caa tat gaa aga gct gaa ggt      672
His Asn Glu Asp Tyr Thr Ile Val Glu Gln Tyr Glu Arg Ala Glu Gly
    210                 215                 220 aga cat tca act ggt ggt atg gat gaa tta tat aaa taa                  711
Arg His Ser Thr Gly Gly Met Asp Glu Leu Tyr Lys
225                 230                 235
```

<210> SEQ ID NO 10
<211> LENGTH: 236
<212> TYPE: PRT
<213> ORGANISM: unknown
<220> FEATURE:
<223> OTHER INFORMATION: Synthetic Construct

<400> SEQUENCE: 10

```
Met Val Ser Lys Gly Glu Glu Asn Asn Met Ala Ile Ile Lys Glu Phe
1               5                   10                  15

Met Arg Phe Lys Val His Val Glu Gly Ser Val Asn Gly His Glu Phe
            20                  25                  30

Glu Ile Glu Gly Glu Gly Glu Gly Arg Pro Tyr Glu Gly Thr Gln Thr
        35                  40                  45

Ala Lys Leu Lys Val Thr Lys Gly Gly Pro Leu Pro Phe Thr Trp Asp
    50                  55                  60

Ile Leu Ser Pro Gln Phe Met Phe Gly Ser Lys Val Tyr Ile Lys His
65                  70                  75                  80

Pro Ala Asp Ile Pro Asp Tyr Phe Lys Leu Ser Phe Pro Glu Gly Phe
                85                  90                  95

Arg Trp Glu Arg Val Met Asn Phe Glu Asp Gly Gly Val Val Thr Val
            100                 105                 110

Thr Gln Asp Ser Ser Leu Gln Asp Gly Val Phe Ile Tyr Lys Val Lys
        115                 120                 125

Leu Arg Gly Thr Asn Phe Pro Ser Asp Gly Pro Val Met Gln Cys Arg
    130                 135                 140

Thr Met Gly Trp Glu Ala Phe Thr Glu Arg Met Tyr Pro Glu Asp Gly
145                 150                 155                 160

Ala Leu Lys Ser Glu Ile Lys Thr Arg Leu Lys Leu Lys Asp Gly Gly
                165                 170                 175
```

```
His Tyr Asp Ala Glu Val Lys Thr Thr Tyr Lys Ala Lys Lys Pro Val
            180                 185                 190

Gln Leu Pro Gly Ala Tyr Asn Val Asp Ile Lys Leu Asp Ile Val Ser
        195                 200                 205

His Asn Glu Asp Tyr Thr Ile Val Glu Gln Tyr Glu Arg Ala Glu Gly
    210                 215                 220

Arg His Ser Thr Gly Gly Met Asp Glu Leu Tyr Lys
225                 230                 235

<210> SEQ ID NO 11
<211> LENGTH: 711
<212> TYPE: DNA
<213> ORGANISM: unknown
<220> FEATURE:
<223> OTHER INFORMATION: synthetic
<220> FEATURE:
<221> NAME/KEY: CDS
<222> LOCATION: (1)..(711)

<400> SEQUENCE: 11 atg gtg agc aag ggc gag gag gat aac atg gcc atc atc aag gag ttc    48
Met Val Ser Lys Gly Glu Glu Asp Asn Met Ala Ile Ile Lys Glu Phe
1               5                   10                  15 atg cgc ttc aag gtg cac atg gag ggc tcc gtg aac ggc cac gag ttc    96
Met Arg Phe Lys Val His Met Glu Gly Ser Val Asn Gly His Glu Phe
            20                  25                  30 gag atc gag ggc gag ggc gag ggc cgc ccc tac gag ggc acc cag acc   144
Glu Ile Glu Gly Glu Gly Glu Gly Arg Pro Tyr Glu Gly Thr Gln Thr
        35                  40                  45 gcc aag ctg aag gtg acc aag ggt ggc ccc ctg ccc ttc gcc tgg gac   192
Ala Lys Leu Lys Val Thr Lys Gly Gly Pro Leu Pro Phe Ala Trp Asp
    50                  55                  60 atc ctg tcc cct cag ttc atg tac ggc tcc aag gcc tac gtg aag cac   240
Ile Leu Ser Pro Gln Phe Met Tyr Gly Ser Lys Ala Tyr Val Lys His
65                  70                  75                  80 ccc gcc gac atc ccc gac tac ttg aag ctg tcc ttc ccc gag ggc ttc   288
Pro Ala Asp Ile Pro Asp Tyr Leu Lys Leu Ser Phe Pro Glu Gly Phe
                85                  90                  95 aag tgg gag cgc gtg atg aac ttc gag gac ggc ggc gtg gtg acc gtg   336
Lys Trp Glu Arg Val Met Asn Phe Glu Asp Gly Gly Val Val Thr Val
            100                 105                 110 acc cag gac tcc tcc ctg cag gac ggc gag ttc atc tac aag gtg aag   384
Thr Gln Asp Ser Ser Leu Gln Asp Gly Glu Phe Ile Tyr Lys Val Lys
        115                 120                 125 ctg cgc ggc acc aac ttc ccc tcc gac ggc ccc gta atg cag aag aag   432
Leu Arg Gly Thr Asn Phe Pro Ser Asp Gly Pro Val Met Gln Lys Lys
    130                 135                 140 acc atg ggc tgg gag gcc tcc tcc gag cgg atg tac ccc gag gac ggc   480
Thr Met Gly Trp Glu Ala Ser Ser Glu Arg Met Tyr Pro Glu Asp Gly
145                 150                 155                 160 gcc ctg aag ggc gag atc aag cag agg ctg aag ctg aag gac ggc ggc   528
Ala Leu Lys Gly Glu Ile Lys Gln Arg Leu Lys Leu Lys Asp Gly Gly
                165                 170                 175 cac tac gac gct gag gtc aag acc acc tac aag gcc aag aag ccc gtg   576
His Tyr Asp Ala Glu Val Lys Thr Thr Tyr Lys Ala Lys Lys Pro Val
            180                 185                 190 cag ctg ccc ggc gcc tac aac gtc aac atc aag ttg gac atc acc tcc   624
Gln Leu Pro Gly Ala Tyr Asn Val Asn Ile Lys Leu Asp Ile Thr Ser
        195                 200                 205 cac aac gag gac tac acc atc gtg gaa cag tac gaa cgc gcc gag ggc   672
His Asn Glu Asp Tyr Thr Ile Val Glu Gln Tyr Glu Arg Ala Glu Gly
```

-continued

```
His Asn Glu Asp Tyr Thr Ile Val Glu Gln Tyr Glu Arg Ala Glu Gly
    210                 215                 220 cgc cac tcc acc ggc ggc atg gac gag ctg tac aag taa                          711
Arg His Ser Thr Gly Gly Met Asp Glu Leu Tyr Lys
225                 230                 235

<210> SEQ ID NO 12
<211> LENGTH: 236
<212> TYPE: PRT
<213> ORGANISM: unknown
<220> FEATURE:
<223> OTHER INFORMATION: Synthetic Construct

<400> SEQUENCE: 12

Met Val Ser Lys Gly Glu Glu Asp Asn Met Ala Ile Ile Lys Glu Phe
1               5                   10                  15

Met Arg Phe Lys Val His Met Glu Gly Ser Val Asn Gly His Glu Phe
                20                  25                  30

Glu Ile Glu Gly Glu Gly Glu Gly Arg Pro Tyr Glu Gly Thr Gln Thr
            35                  40                  45

Ala Lys Leu Lys Val Thr Lys Gly Gly Pro Leu Pro Phe Ala Trp Asp
    50                  55                  60

Ile Leu Ser Pro Gln Phe Met Tyr Gly Ser Lys Ala Tyr Val Lys His
65                  70                  75                  80

Pro Ala Asp Ile Pro Asp Tyr Leu Lys Leu Ser Phe Pro Glu Gly Phe
                85                  90                  95

Lys Trp Glu Arg Val Met Asn Phe Glu Asp Gly Gly Val Val Thr Val
            100                 105                 110

Thr Gln Asp Ser Ser Leu Gln Asp Gly Glu Phe Ile Tyr Lys Val Lys
        115                 120                 125

Leu Arg Gly Thr Asn Phe Pro Ser Asp Gly Pro Val Met Gln Lys Lys
    130                 135                 140

Thr Met Gly Trp Glu Ala Ser Ser Glu Arg Met Tyr Pro Glu Asp Gly
145                 150                 155                 160

Ala Leu Lys Gly Glu Ile Lys Gln Arg Leu Lys Leu Lys Asp Gly Gly
                165                 170                 175

His Tyr Asp Ala Glu Val Lys Thr Thr Tyr Lys Ala Lys Lys Pro Val
            180                 185                 190

Gln Leu Pro Gly Ala Tyr Asn Val Asn Ile Lys Leu Asp Ile Thr Ser
        195                 200                 205

His Asn Glu Asp Tyr Thr Ile Val Glu Gln Tyr Glu Arg Ala Glu Gly
    210                 215                 220

Arg His Ser Thr Gly Gly Met Asp Glu Leu Tyr Lys
225                 230                 235
```